(12) United States Patent
Koishihara et al.

(10) Patent No.: US 6,503,510 B2
(45) Date of Patent: *Jan. 7, 2003

(54) REMEDIES FOR LYMPHOCYTIC TUMORS

(75) Inventors: Yasuo Koishihara, Gotenba (JP); Yasushi Yoshimura, Gotenba (JP)

(73) Assignee: Chugai Seiyaku Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,925

(22) PCT Filed: Feb. 12, 1998

(86) PCT No.: PCT/JP98/00568

§ 371 (c)(1),
(2), (4) Date: Aug. 11, 1999

(87) PCT Pub. No.: WO98/35698

PCT Pub. Date: Aug. 20, 1998

(65) Prior Publication Data

US 2002/0037288 A1 Mar. 28, 2002

(30) Foreign Application Priority Data

Feb. 12, 1997 (JP) ............................................ 9-041410

(51) Int. Cl.$^7$ ............................................ A61K 39/395
(52) U.S. Cl. .................. 424/156.1; 530/387.1; 530/387.3; 530/388.85; 424/133.1
(58) Field of Search ............................ 530/387.1, 387.3, 530/388.1, 388.8, 388.85; 424/130.1, 133.9, 139.1, 141.1, 155.1, 156.1

(56) References Cited

U.S. PATENT DOCUMENTS 5,650,150 A * 7/1997 Gillies

FOREIGN PATENT DOCUMENTS

| EP | 0 628 639 | 12/1994 |
|----|-----------|---------|
| EP | 0 733 643 | 9/1996 |
| EP | 0 960 936 | 12/1999 |
| EP | 0 972 524 | 1/2000 |
| EP | 1 020 522 | 7/2000 |
| EP | 1 023 906 | 8/2000 |

OTHER PUBLICATIONS

Paul, Fundamental immunology Chapter 8, Raven Press NY, p. 242, 1993.*
Riechmann et al., Nature 332:323–327, 1988.*
Jain, Sci. Amer. 271:58, 1994.*
Chatterjee et al., Cancer Immunol. Immunother. 38:75–82, 1994.*
Gura, Science 278:1041–1042, 1997.*
Knight., Bio Technology 7, No. 1, 1989.*
Greenspan et al., Nature Biotechnology 17:936–937, 1999.*
Goto, et al., "A Novel Membrane Antigen Selectively Expressed on Terminally Differentiated Human B Cells," Blood, col. 84, No. 6, 1922–1930 (1994).
Ozaki, et al., "Localization and Imaging of Human Plasmacytoma Xenografts in Severe Combined Immunodeficiency Mice by a New Murine Monoclonal Antibody, ANTI–HM1.24," Tokushima Jouranl of Experimental Medicine, vol. 43, 7–15 (1996).
Ozaki, et al., "Immunotherapy of Multiple Myeloma With a Monoclonal Antibody Directed Against a Plasma Cell–Specific Antigen, HM1.24," Blook, vol. 90, No. 8, 3179–3186 (1997).
Ozaki et al.; "Localization and Imaging of Human Plasmacytoma Xenografts in Severe Combined Immunodeficiency Mice by A New Murine Monoclonal Antibody, Anti–HM1.24", Radiolocalization of Human Plasmacytoma; Tokushima Journal of Experimental Medicine; vol. 43; 1996 pp. 7–15; XP002912306.
Chatterjee et al.; "Idiotypic Antibody Immunotheraphy of Cancer"; Immunotherapy; Springer–Verlag; vol. 38; 1994; pp. 75–82.
Paul et al.; Fundamental Immunology; Raven Press NY; 1993; p242.
Jain; "Barriers to Drug Delivery in Solid Tumors"; Scientific American; vol. 271, No. 1; Jul. 1994; pp. 58–65.
Gura Cancer Models; "System for Identifying New Drugs Are Often Faulty"; Science; vol. 278; Nov. 7, 1997; pp. 1041–1042.
Knight; "The Carbohydrate Frontier"; Biotechnology Nature Publishing; vol. 7, No. 1; Jan. 1989; 4 Sheets.
Greenspan et al.; "Defining Epitopes: It's Not As Easy As It Seems"; Nature Biotechnology; vol. 17; Oct. 1999; pp. 236–237.

* cited by examiner

Primary Examiner—Sheela Huff
Assistant Examiner—Larry R. Helms
(74) Attorney, Agent, or Firm—Foley & Lardner

(57) ABSTRACT

A therapeutic agent for lymphatic tumors (excluding myeloma) comprising as an active ingredient an antibody that specifically binds to a protein having the amino acid sequence as set forth in SEQ ID NO:1 and SEQ ID NO:5 and that has a cytotoxic activity.

12 Claims, 27 Drawing Sheets

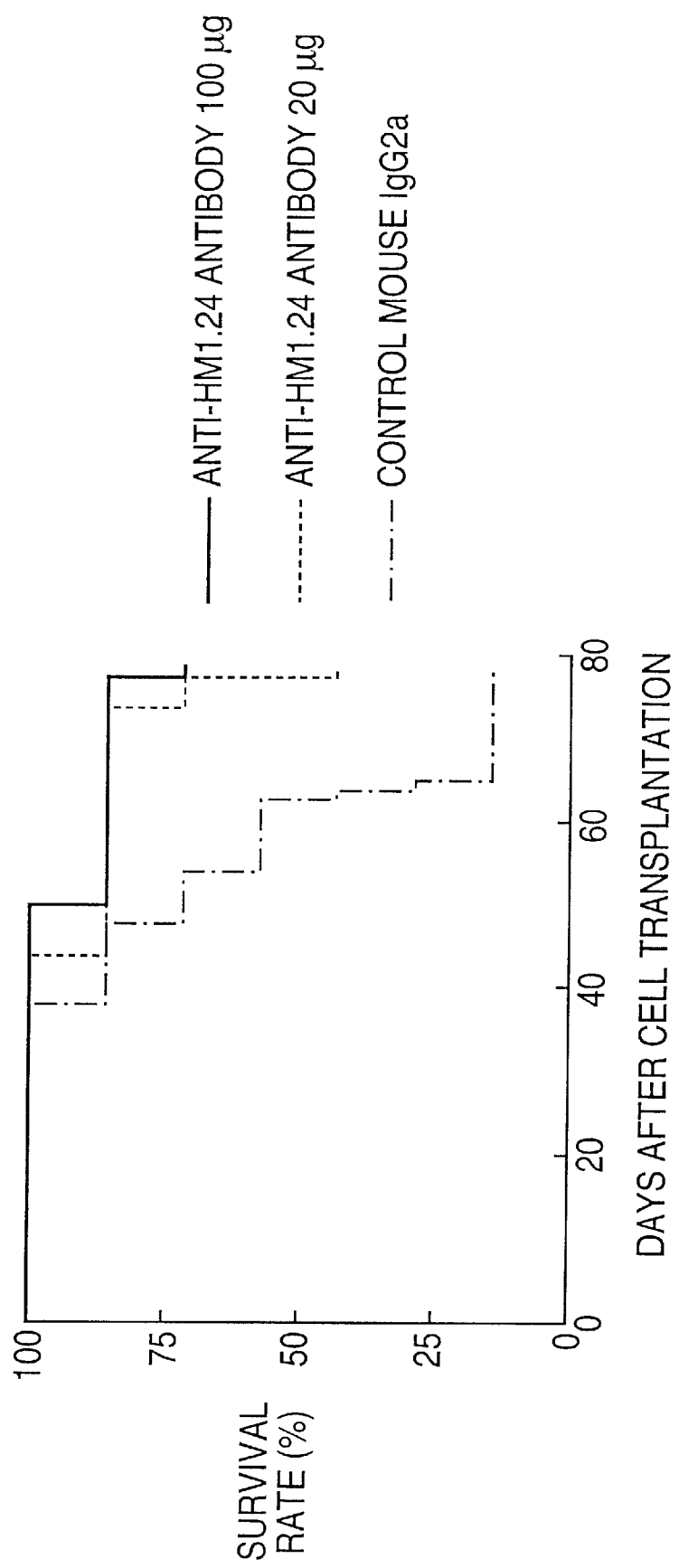

REMEDIES FOR LYMPHOCYTIC TUMORS

TECHNICAL FIELD

The present invention relates to therapeutic agents for lymphatic tumors (excluding myeloma) comprising as an active ingredient antibodies that specifically bind to proteins expressed in said lymphatic tumors. The present invention also relates to therapeutic agents for T cell tumors or B cell tumors (excluding myeloma). Furthermore, the present invention relates to antibodies that specifically bind to proteins expressed in lymphatic tumors and that have a cytotoxic activity.

BACKGROUND ART

Lymphatic cells are mainly responsible for immunity in the living body. Lymphatic cells are all derived from the same hemopoietic stem cells, which are released into the peripheral blood after repeated differentiation by the action of various differentiation inducing factors or growth factors in the bone marrow or other organs. Due to differences in such differentiation, lymphocytes are broadly classified into the B cells and the T cells. The B cells are thought to have the ability of producing antibodies whereas the T cells are thought to have the ability of antigen presentation, cytotoxicity and the like. When these cells undergo tumorigenic change for some reason or other during certain stages of differentiation and begin to proliferate in an uncontrolled manner in the bone marrow, the lymphatic tissues, the blood or the like, such a state is called a lymphatic tumor.

Because of the introduction of new technologies, in particular technological advances that make use of monoclonal antibodies against differentiation antigens on the cell surface, it has become possible to identify the origin and/or the differentiation stage of lymphatic cells. Accompanied by this, it has also become possible not only to determine whether such tumor cells are derived from T cells or B cells but also to identify the degree of maturity of tumor cells.

Lymphatic tumors are broadly classified into the B cell tumors and the T cell tumors based on the origin and degree of maturity of tumor cells. Based on the degree of maturity of tumor cells, the B cell tumors are classified into acute B lymphatic leukemia (B-ALL), chronic B lymphatic leukemia (B-CLL), pre-B lymphoma, Burkitt lymphoma, follicular lymphoma, follicular pallium lymphoma, diffuse lymphoma and the like. On the other hand, the T cell tumors are classified, based on the degree of maturity of tumor cells, into acute T lymphatic leukemia (T-ALL), chronic T lymphatic leukemia (T-CLL), adult T cell leukemia (ATL), non-ATL peripheral T lymphoma (PNTL) and the like (Zukai Rinsho [Gan] (Illustrated Clinical: Cancer), series No. 17 Leukemia and lymphoma, Takashi Sugimura et al., Medical View Co., Ltd., 1987, B cell tumors, Kiyoshi Takatsuki, Nishimura Shoten, 1991).

It is true that, despite recent advances in the medical technologies, treatments of lymphatic tumors are not satisfactory. The cure rate of acute lymphatic leukemia (ALL), for example, is still 20% or lower, and that of lymphoma is still about 50% at the advanced stage although the cure rate for B lymphoma is said to be relatively high due to the progress of multi-drug therapies. Furthermore, T lymphoma is more intractable and has a cure rate of about 30%, and the rate is under 10% for adult T cell leukemia (ATL) at present.

On the other hand, Goto, T. et al. have reported a monoclonal antibody (anti-HM1.24 antibody) that was obtained by immunizing mice with human myeloma cells (Blood (1994) 84, 1922–1930). When anti-HM1.24 antibody was administered to a mouse transplanted with human myeloma cells, the antibody accumulated in tumor tissues in a specific manner (Masaaki Kosaka et al., Nippon Rinsho (Japan Clinical) (1995) 53, 627–635), suggesting that anti-HM1.24 antibody could be applied in the diagnosis of tumor localization by radioisotopic labeling, missile therapies such as radioimmunotherapy, and the like. However, it is not known that anti-HM1.24 antibody is useful for treatment of other lymphatic tumors.

DISCLOSURE OF THE INVENTION

Therapeutic methods for lymphatic tumors that are currently used include various chemotherapies, X-ray therapies, bone marrow transplantation and the like. As mentioned above, however, none of these are yet satisfactory for the diseases, and thus epoch-making therapeutic agents or methods that can alleviate lymphatic tumors and prolong the survival period of the patient are being awaited.

Thus, it is an object of the present invention to provide a new therapeutic agent for lymphatic tumors excluding myeloma.

In order to provide such a therapeutic agent, the inventors have extensively conducted in vitro studies including flow cytometry (FCM) analysis, determination of cytotoxic activities such as an ADCC activity, a CDC activity, etc. and in vivo studies on antitumor effects using anti-HM1.24 antibody (Goto, T. et al., Blood (1994) 84, 1922–1930), and studies on the isolation of the antigen protein to which anti-HM1.24 antibody specifically binds. As a result, the inventors have found that the antigen protein recognized by anti-HM1.24 antibody is being expressed on lymphatic tumors and that anti-HM1.24 antibody has an antitumor effect on lymphatic tumors, and thereby have completed the present invention.

Thus, the present invention provides a therapeutic agent for lymphatic tumors (excluding myeloma) comprising as an active ingredient an antibody that specifically binds to a protein having the amino acid sequence as set forth in SEQ ID NO:1 and SEQ ID NO:5 and that has a cytotoxic activity.

The present invention also provides a therapeutic agent for T cell tumors or a therapeutic agent for B cell tumors (excluding myeloma) comprising as an active ingredient an antibody that specifically binds to a protein having the amino acid sequence as set forth in SEQ ID NO:1 and SEQ ID NO:5 and that has a cytotoxic activity.

The present invention also provides a therapeutic agent for T cell tumors or a therapeutic agent for B cell tumors (excluding myeloma) comprising as an active ingredient a monoclonal antibody that specifically binds to a protein having the amino acid sequence as set forth in SEQ ID NO:1 and SEQ ID NO:5 and that has a cytotoxic activity.

The present invention also provides a therapeutic agent for T cell tumors or a therapeutic agent for B cell tumors (excluding myeloma) comprising as an active ingredient an antibody that specifically binds to a protein having the amino acid sequence as set forth in SEQ ID NO:1 and that has an ADCC activity or a CDC activity as the cytotoxic activity.

The present invention also provides a therapeutic agent for T cell tumors or a therapeutic agent for B cell tumors (excluding myeloma) comprising as an active ingredient an antibody that specifically binds to a protein having the amino acid sequence as set forth in SEQ ID NO:1 and SEQ ID NO:5, that has a cytotoxic activity, and that has Cγ of human antibody as the constant region.

The present invention also provides a therapeutic agent for T cell tumors or a therapeutic agent for B cell tumors (excluding myeloma) comprising as an active ingredient a chimeric antibody or a humanized antibody that specifically binds to a protein having the amino acid sequence as set forth in SEQ ID NO:1 and SEQ ID NO:5 and that has a cytotoxic activity.

The present invention also provides a therapeutic agent for T cell tumors or a therapeutic agent for B cell tumors (excluding myeloma) comprising as an active ingredient an antibody that specifically binds to an epitope recognized by anti-HM1.24 antibody.

The present invention also provides a therapeutic agent for T cell tumors or a therapeutic agent for B cell tumors (excluding myeloma) comprising anti-HM1.24 antibody as an active ingredient.

Furthermore, the present invention relates to an antibody that specifically binds to a protein expressed on lymphatic tumors and that has a cytotoxic activity.

BRIEF DESCRIPTION OF THE DRAWINGS

FIG. 1 shows a histogram of FCM analysis of the indicated B cell line by the indirect method using anti-HM1.24 antibody and control mouse IgG2a.

FIG. 2 shows a histogram of the indicated B cell line that was FCM analyzed by the indirect method using anti-HM1.24 antibody and control mouse IgG2a.

FIG. 3 shows a histogram of the indicated B cell line that was FCM analyzed by the indirect method using anti-HM1.24 antibody and control mouse IgG2a.

FIG. 4 shows a histogram of the indicated B cell line that was FCM analyzed by the indirect method using anti-HM1.24 antibody and control mouse IgG2a.

FIG. 5 shows a histogram of the indicated B cell line that was FCM analyzed by the indirect method using anti-HM1.24 antibody and control mouse IgG2a.

FIG. 6 shows a histogram of the indicated B cell line that was FCM analyzed by the indirect method using anti-HM1.24 antibody and control mouse IgG2a.

FIG. 7 shows a histogram of the indicated B cell line that was FCM analyzed by the indirect method using anti-HM1.24 antibody and control mouse IgG2a.

FIG. 8 shows a histogram of the indicated B cell line that was FCM analyzed by the indirect method using anti-HM1.24 antibody and control mouse IgG2a.

FIG. 9 shows a histogram of the indicated B cell line that was FCM analyzed by the indirect method using anti-HM1.24 antibody and control mouse IgG2a.

FIG. 10 shows a histogram of the indicated T cell line that was FCM analyzed by the indirect method using anti-HM1.24 antibody and control mouse IgG2a.

FIG. 11 shows a histogram of the indicated T cell line that was FCM analyzed by the indirect method using anti-HM1.24 antibody and control mouse IgG2a.

FIG. 12 shows a histogram of the indicated T cell line that was FCM analyzed by the indirect method using anti-HM1.24 antibody and control mouse IgG2a.

FIG. 13 shows a histogram of the indicated T cell line that was FCM analyzed by the indirect method using anti-HM1.24 antibody and control mouse IgG2a.

FIG. 14 shows a histogram of the indicated T cell line that was FCM analyzed by the indirect method using anti-HM1.24 antibody and control mouse IgG2a.

FIG. 15 shows a histogram of the indicated T cell line that was FCM analyzed by the indirect method using anti-HM1.24 antibody and control mouse IgG2a.

FIG. 16 shows a histogram of the indicated T cell line that was FCM analyzed by the indirect method using anti-HM1.24 antibody and control mouse IgG2a.

FIG. 17 shows a histogram of the indicated T cell line that was FCM analyzed by the indirect method using anti-HM1.24 antibody and control mouse IgG2a.

FIG. 18 shows a histogram of the indicated T cell line that was FCM analyzed by the indirect method using anti-HM1.24 antibody and control mouse IgG2a.

FIG. 19 shows a histogram of the indicated T cell line that was FCM analyzed by the indirect method using anti-HM1.24 antibody and control mouse IgG2a.

FIG. 20 shows a histogram of the indicated non-T, non-B cell line that was FCM analyzed by the indirect method using anti-HM1.24 antibody and control mouse IgG2a.

FIG. 21 shows a histogram of the indicated non-T, non-B cell line that was FCM analyzed by the indirect method using anti-HM1.24 antibody and control mouse IgG2a.

FIG. 22 shows a histogram of the indicated non-T, non-B cell line that was FCM analyzed by the indirect method using anti-HM1.24 antibody and control mouse IgG2a.

FIG. 23 shows a histogram of the indicated non-T, non-B cell line that was FCM analyzed by the indirect method using anti-HM1.24 antibody and control mouse IgG2a.

FIG. 27 is a graph showing that the survival period has been extended in the anti-HM1.24 antibody administration group as compared to the control mouse IgG2a administration group in mice transplanted with a human lymphatic tumor.

EMBODIMENT FOR CARRYING OUT THE INVENTION

1. Antibody Preparation 1-1. Hybridoma preparation

Figure 1:
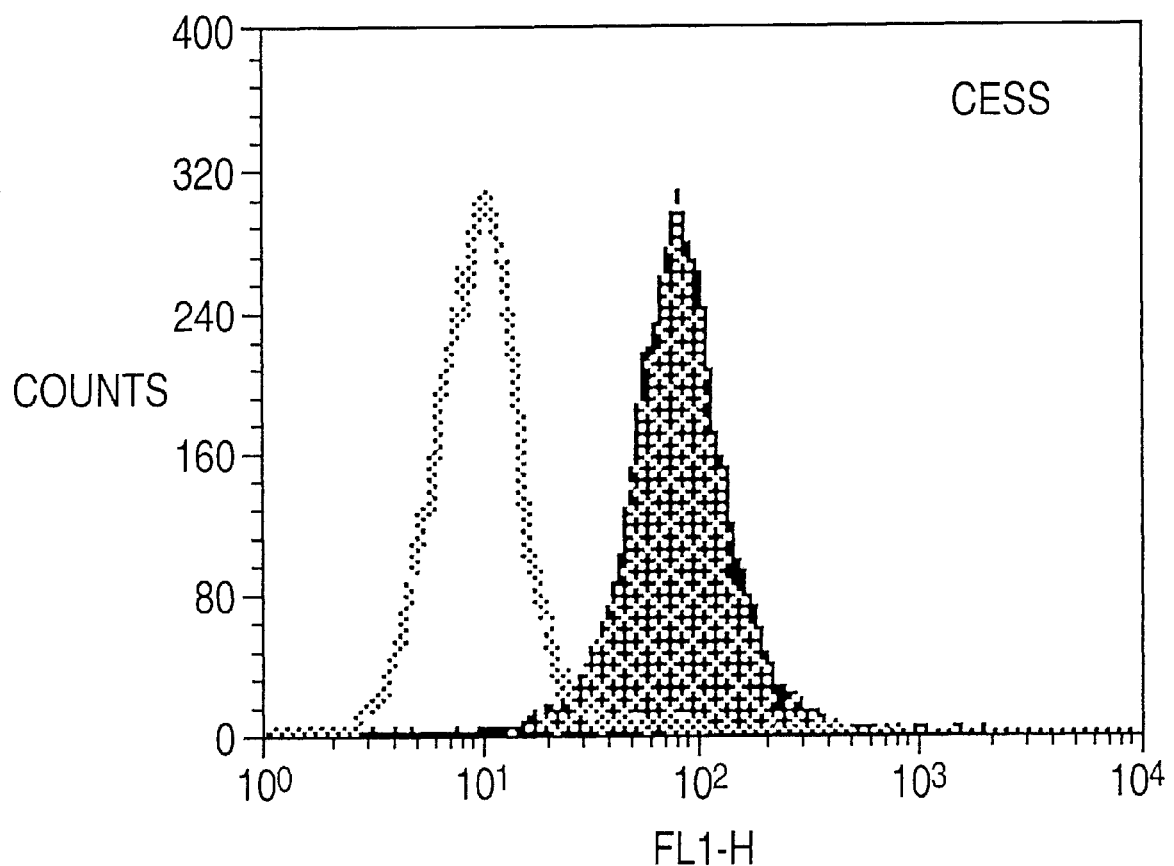
Figure 2:
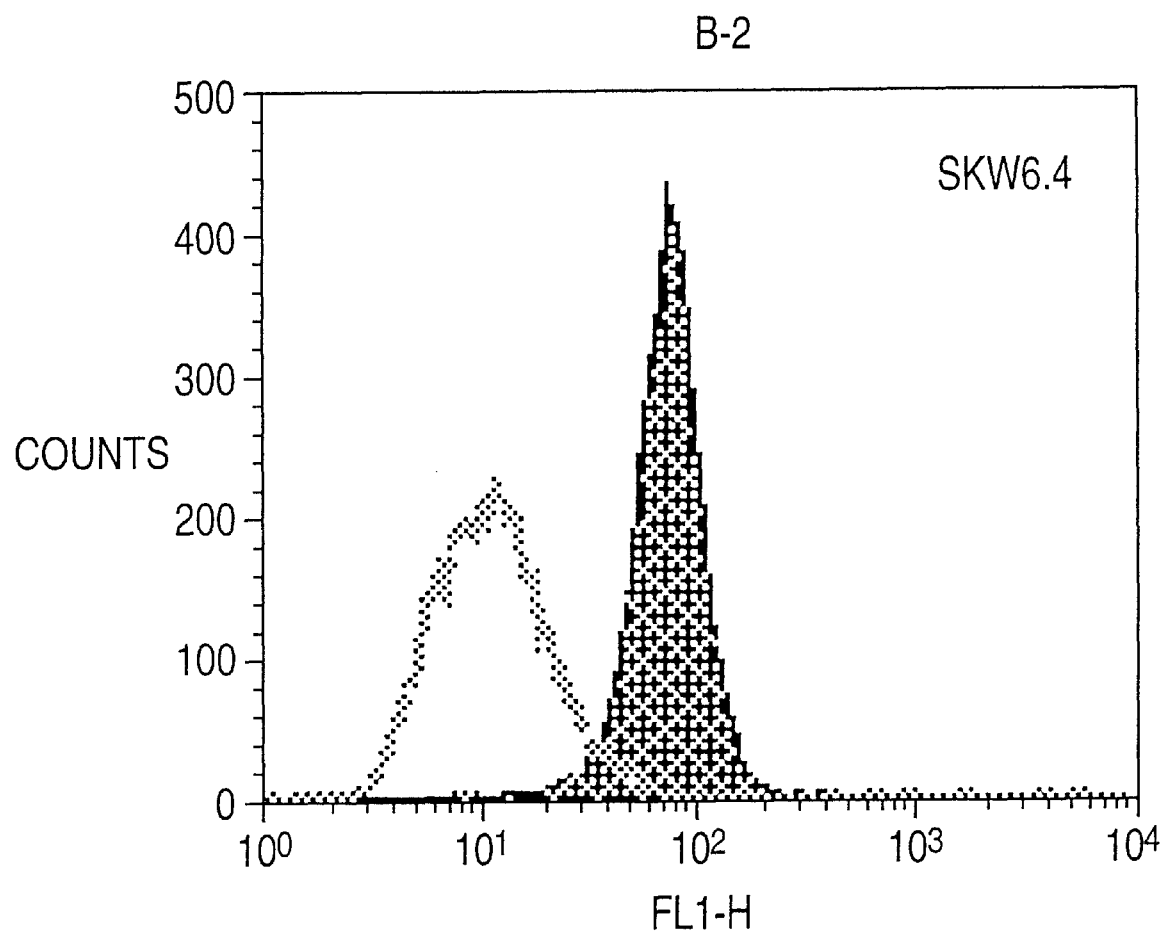
Figure 3:
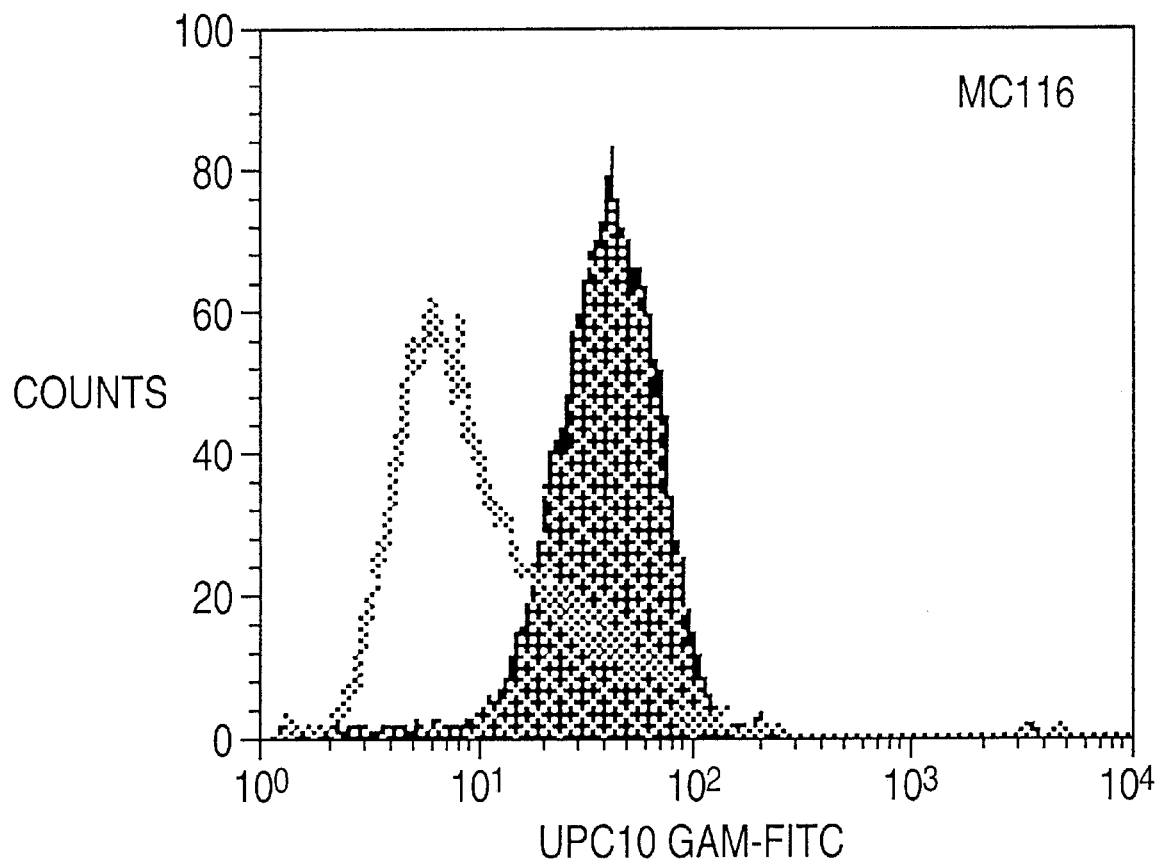
Figure 4:
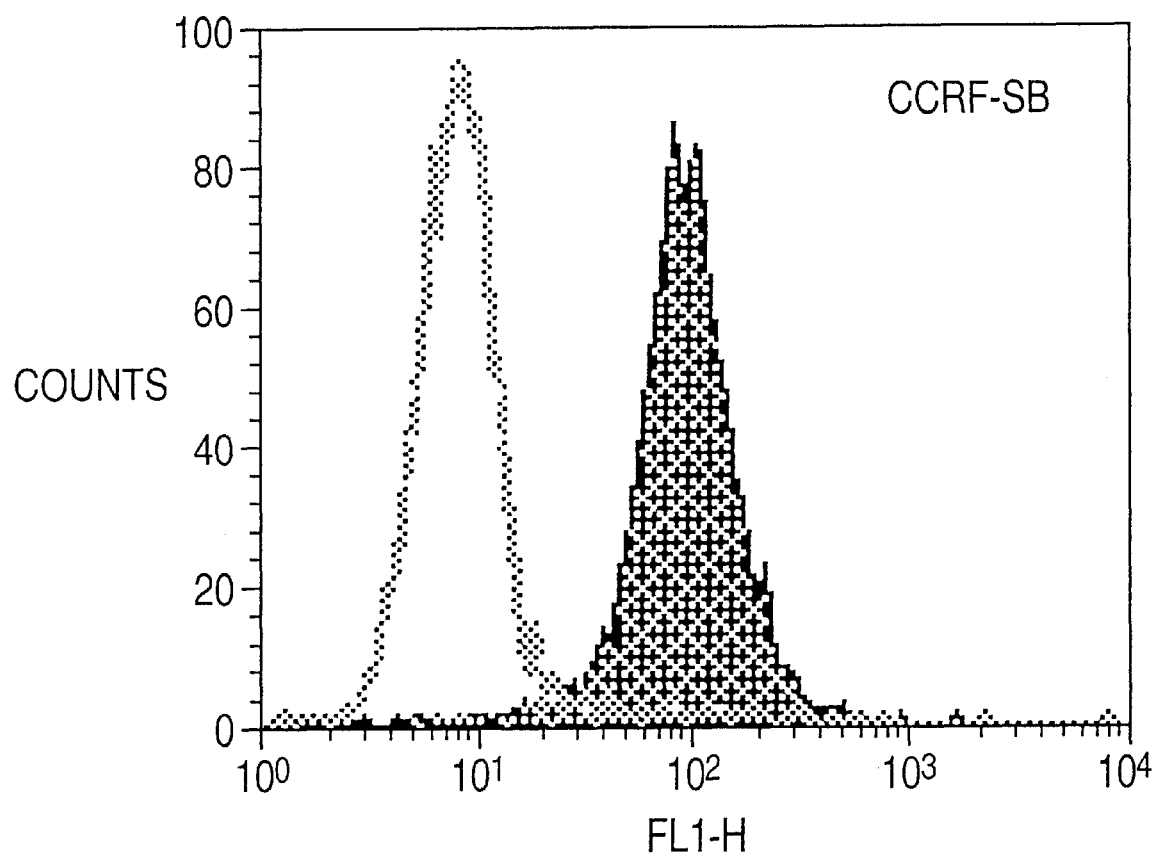
Figure 5:
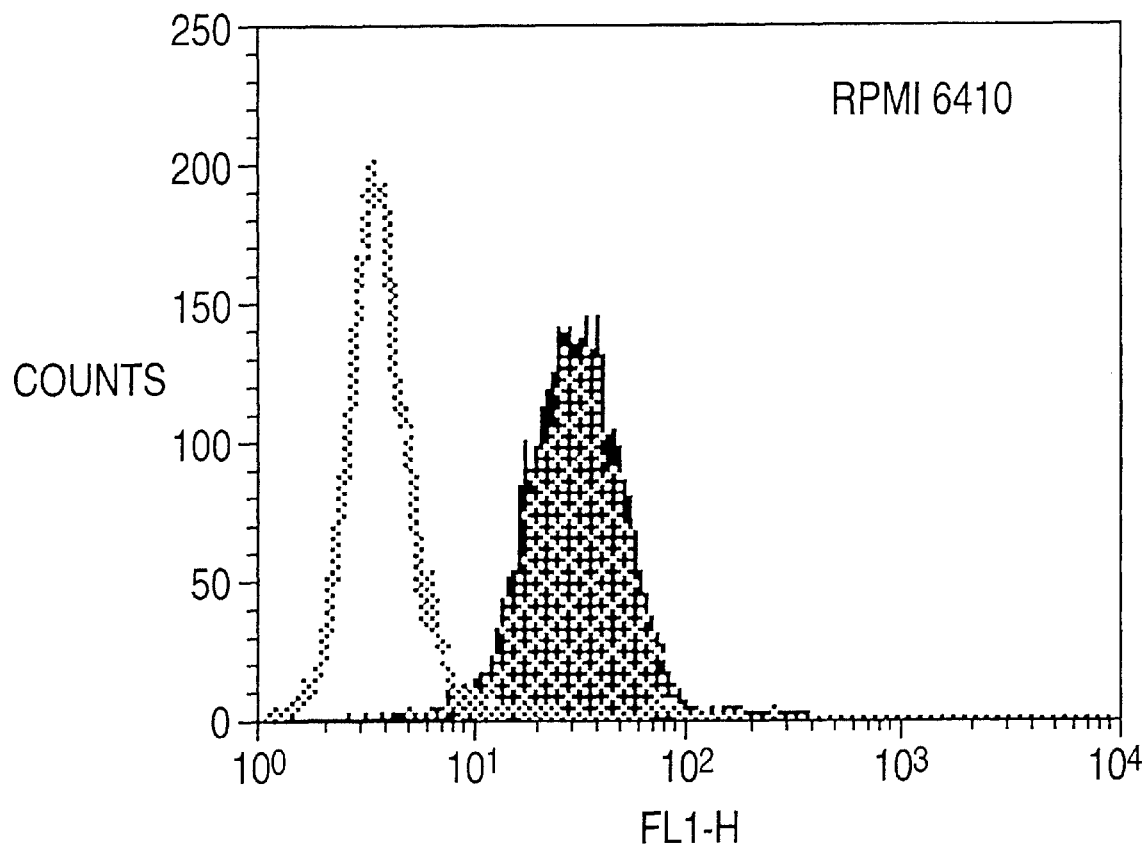
Figure 6:
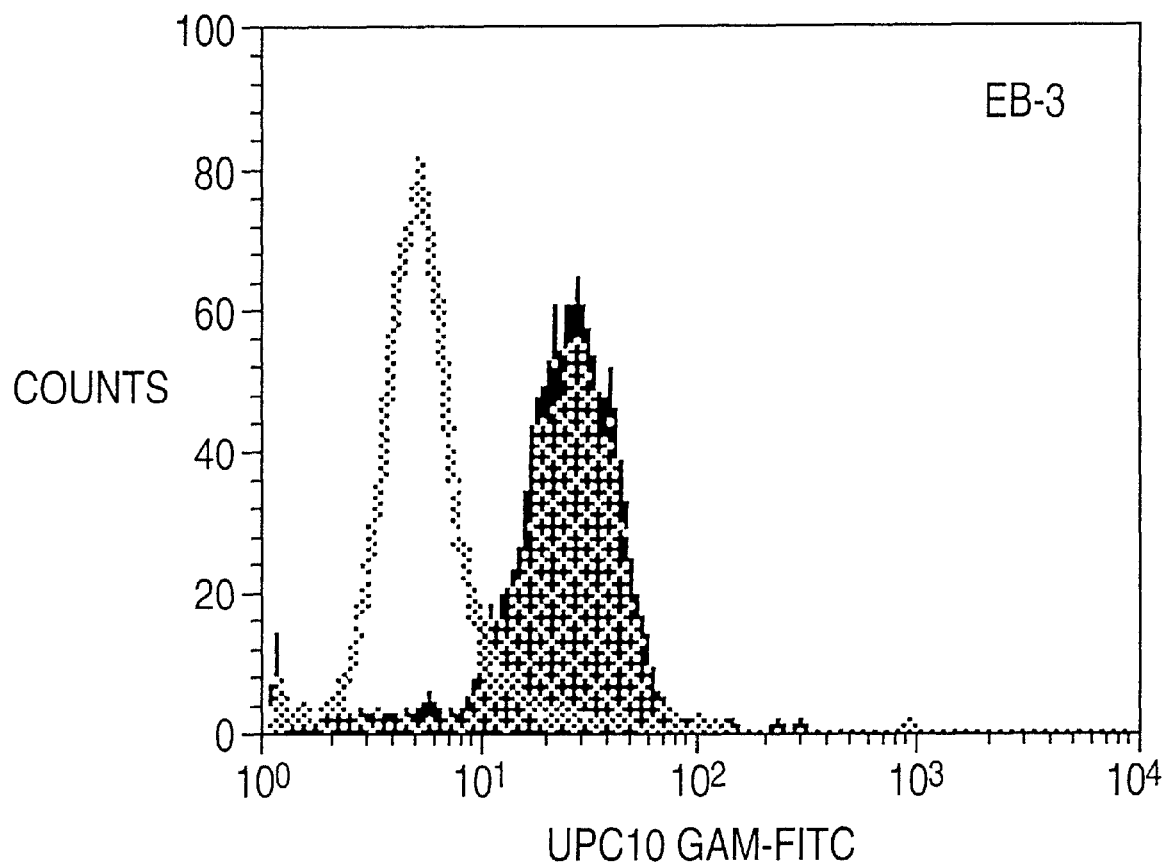
Figure 7:
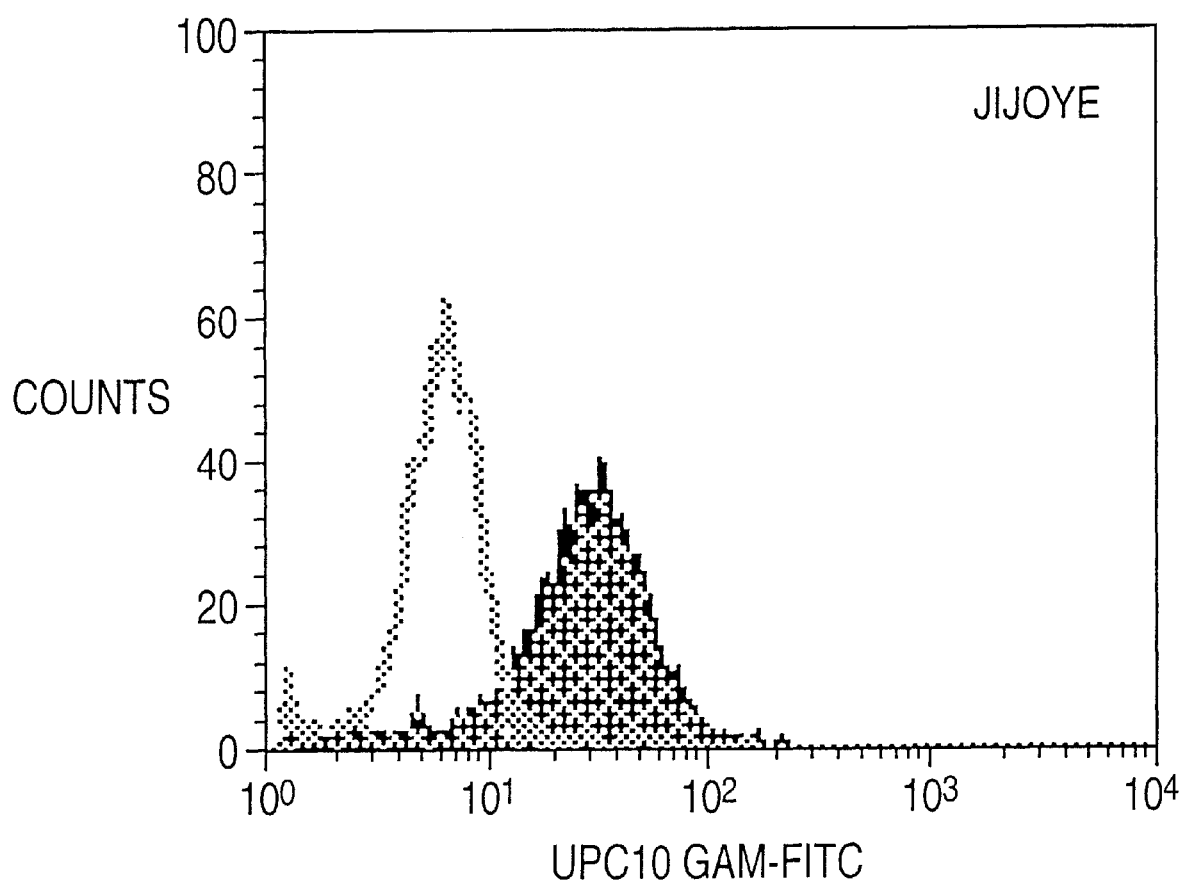
Figure 8:
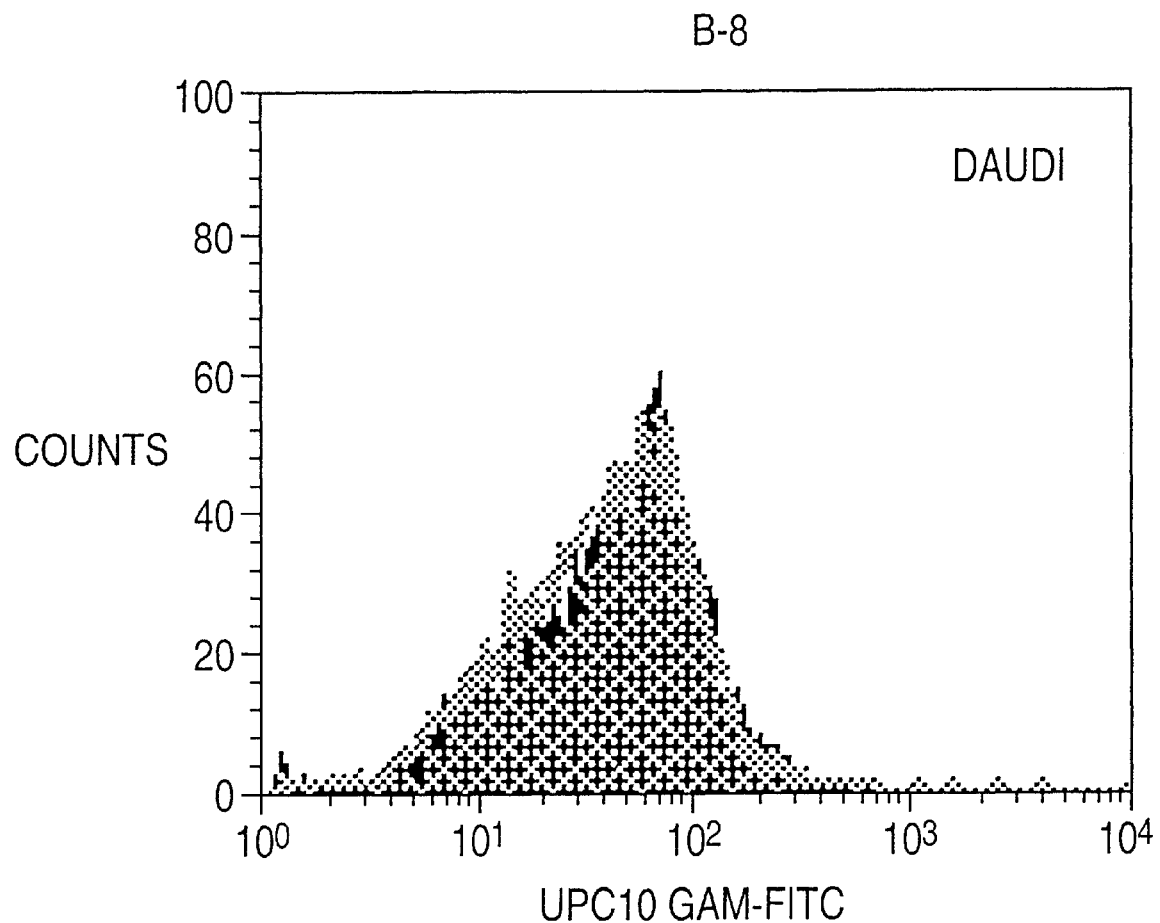
Figure 9:
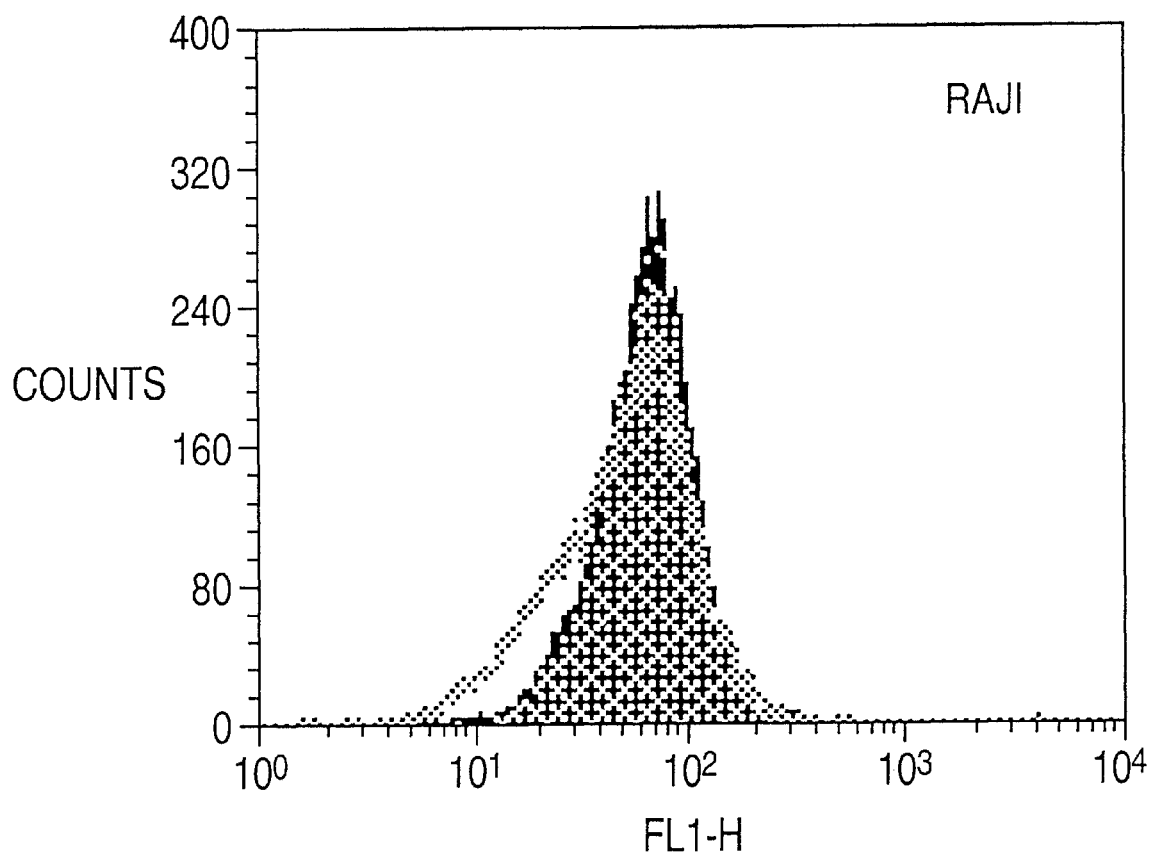
Figure 10:
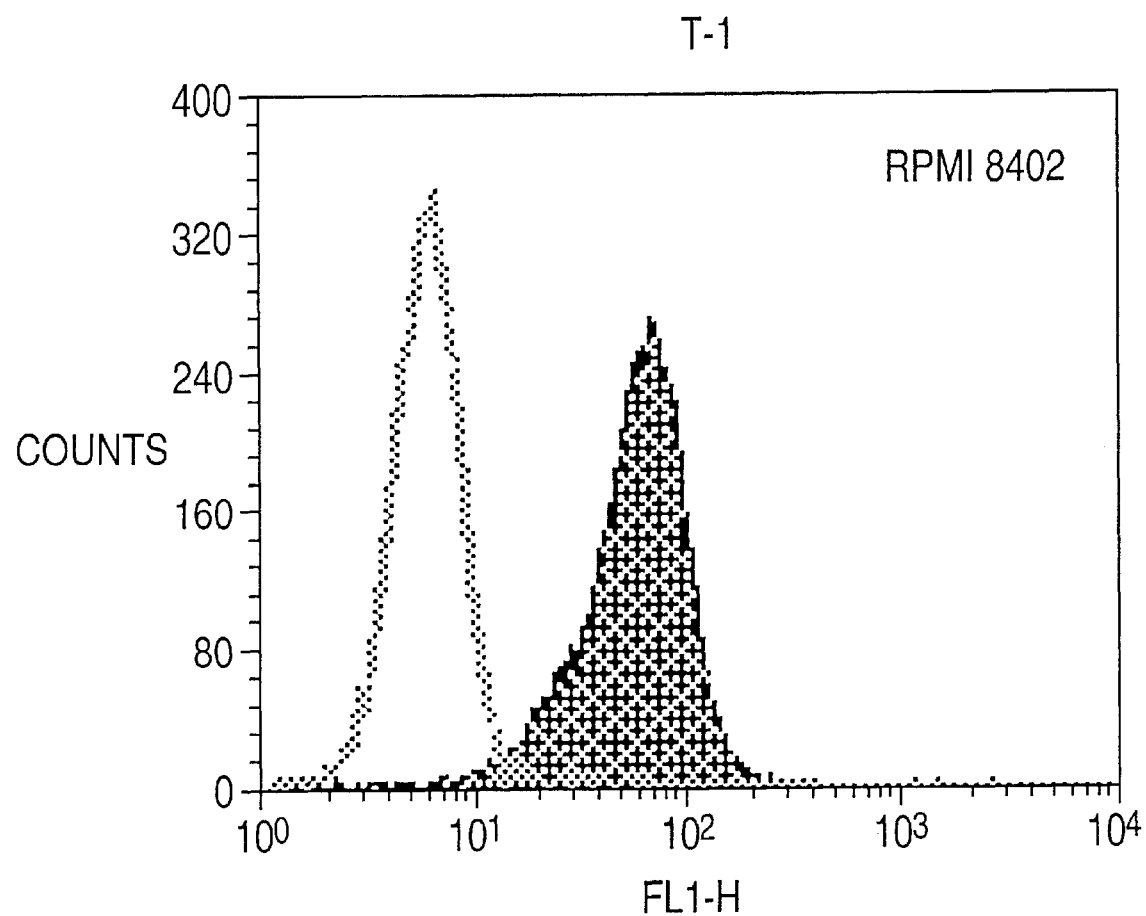
Figure 11:
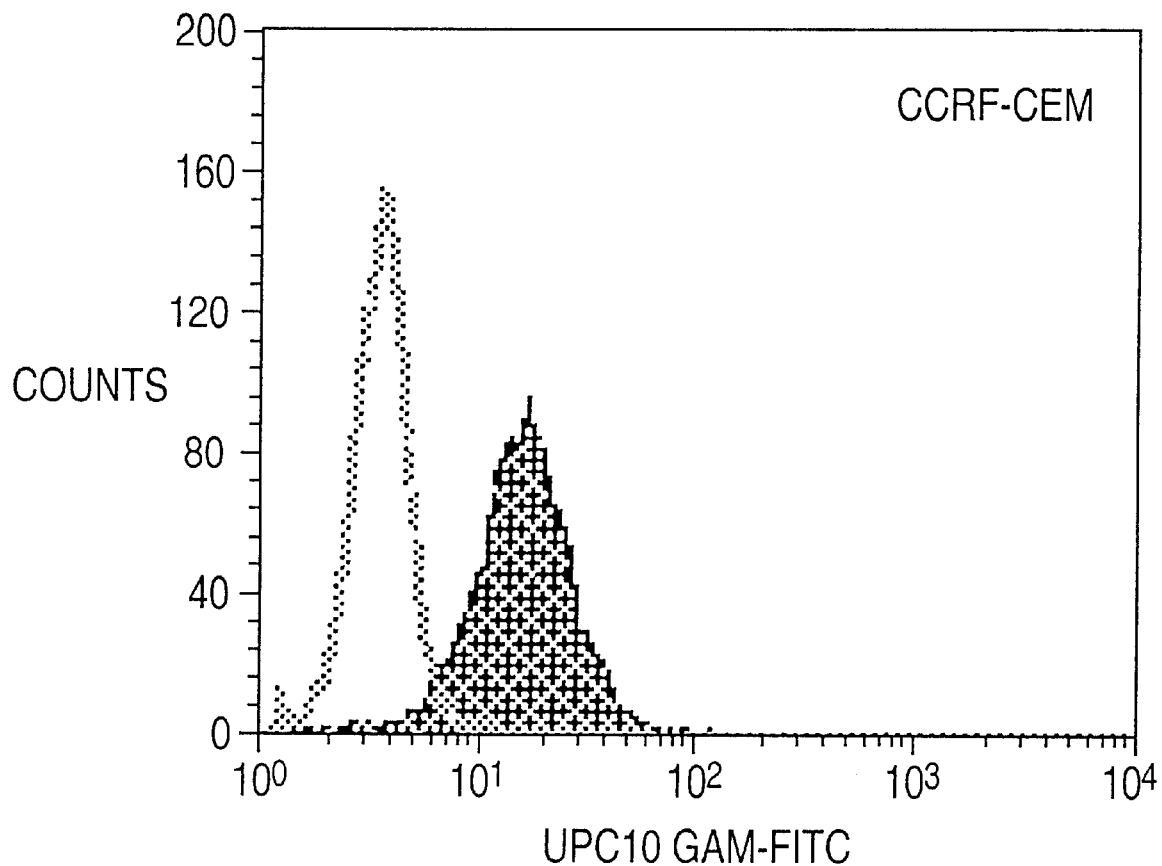
Figure 12:
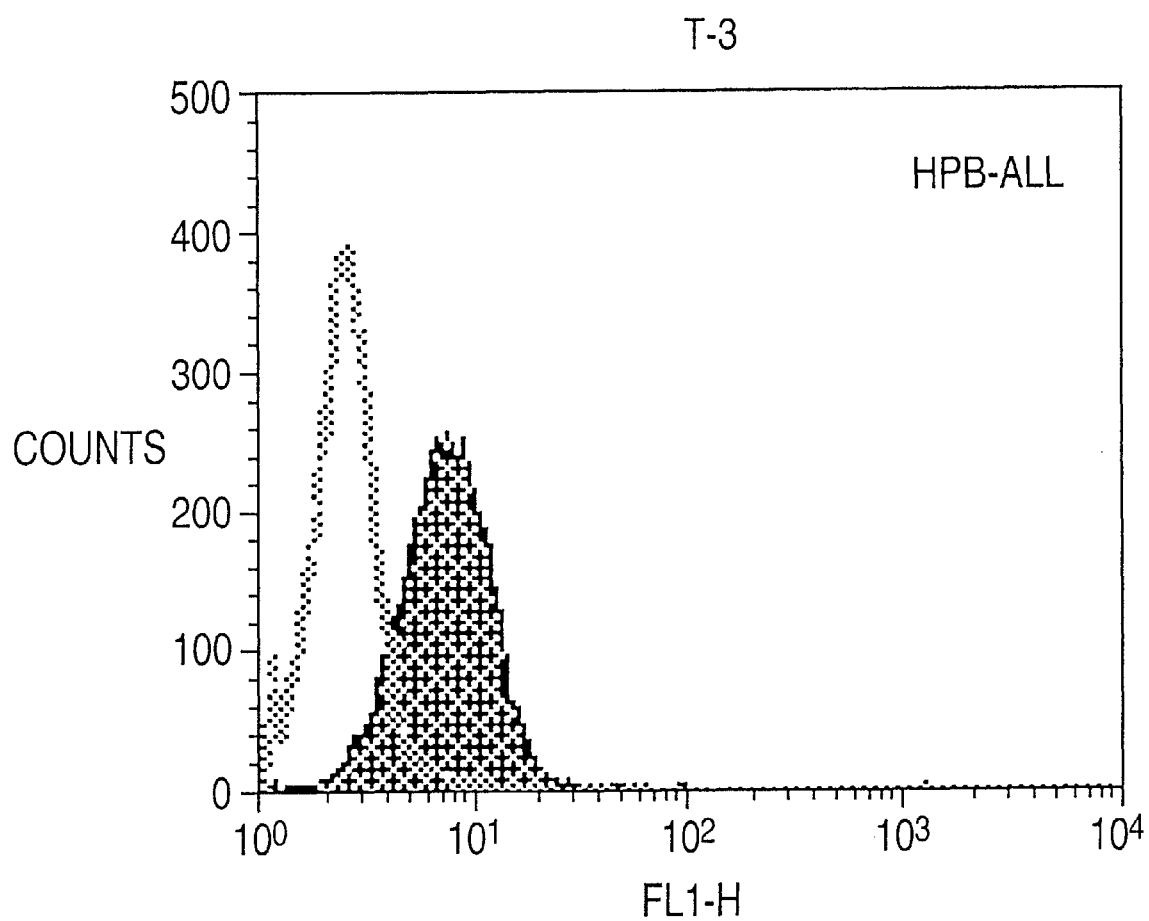
Figure 13:
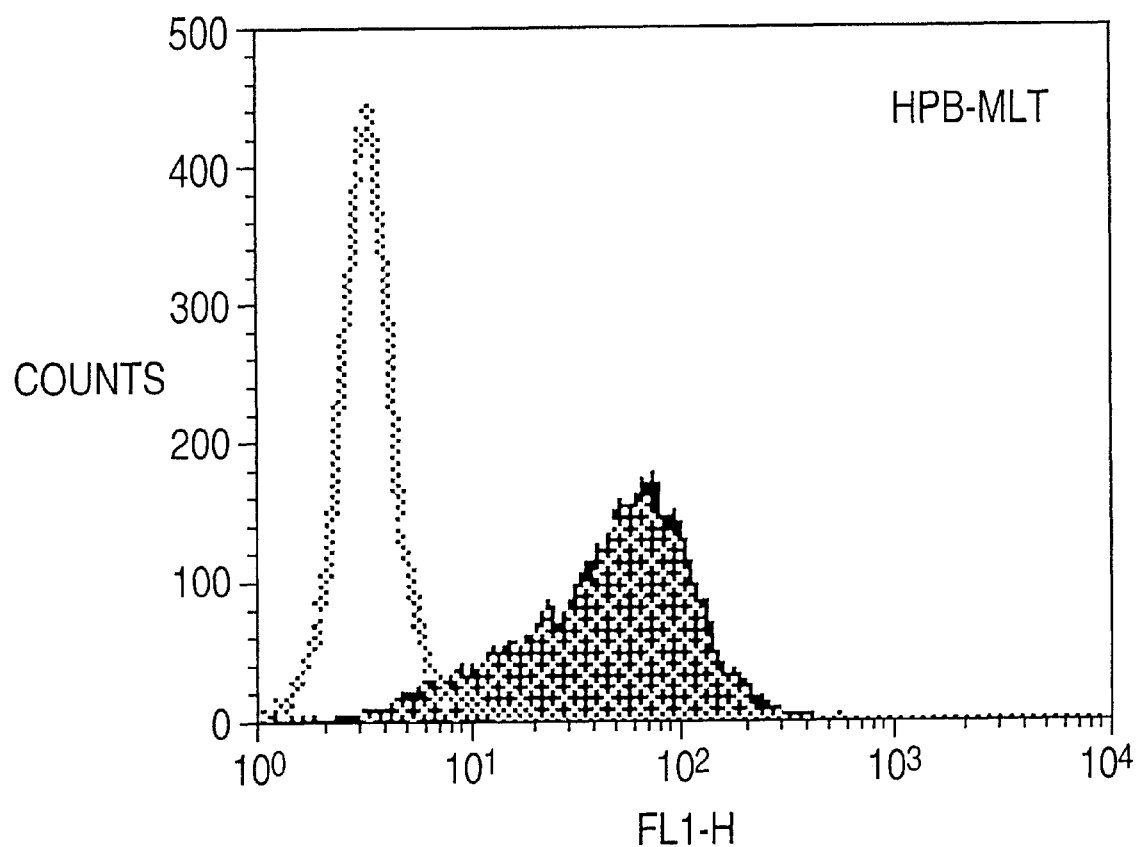
Figure 14:
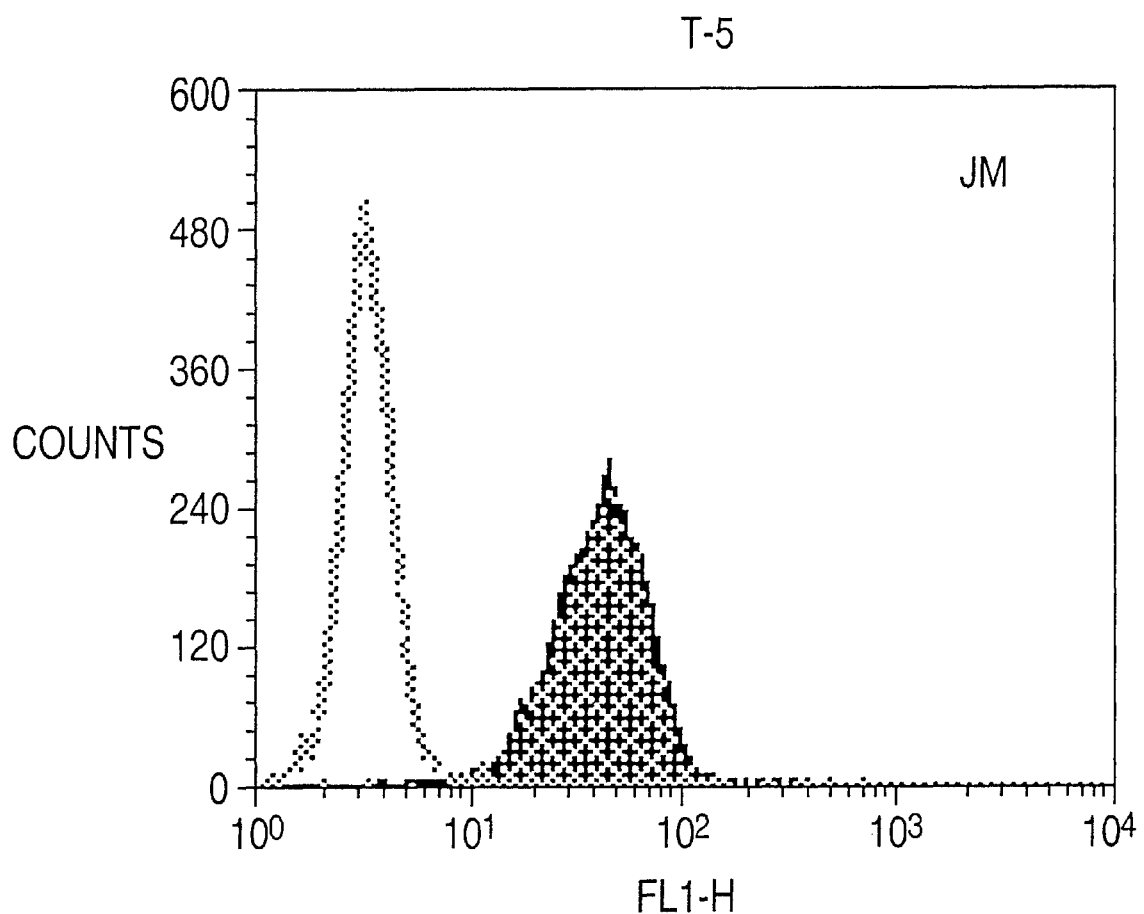
Figure 15:
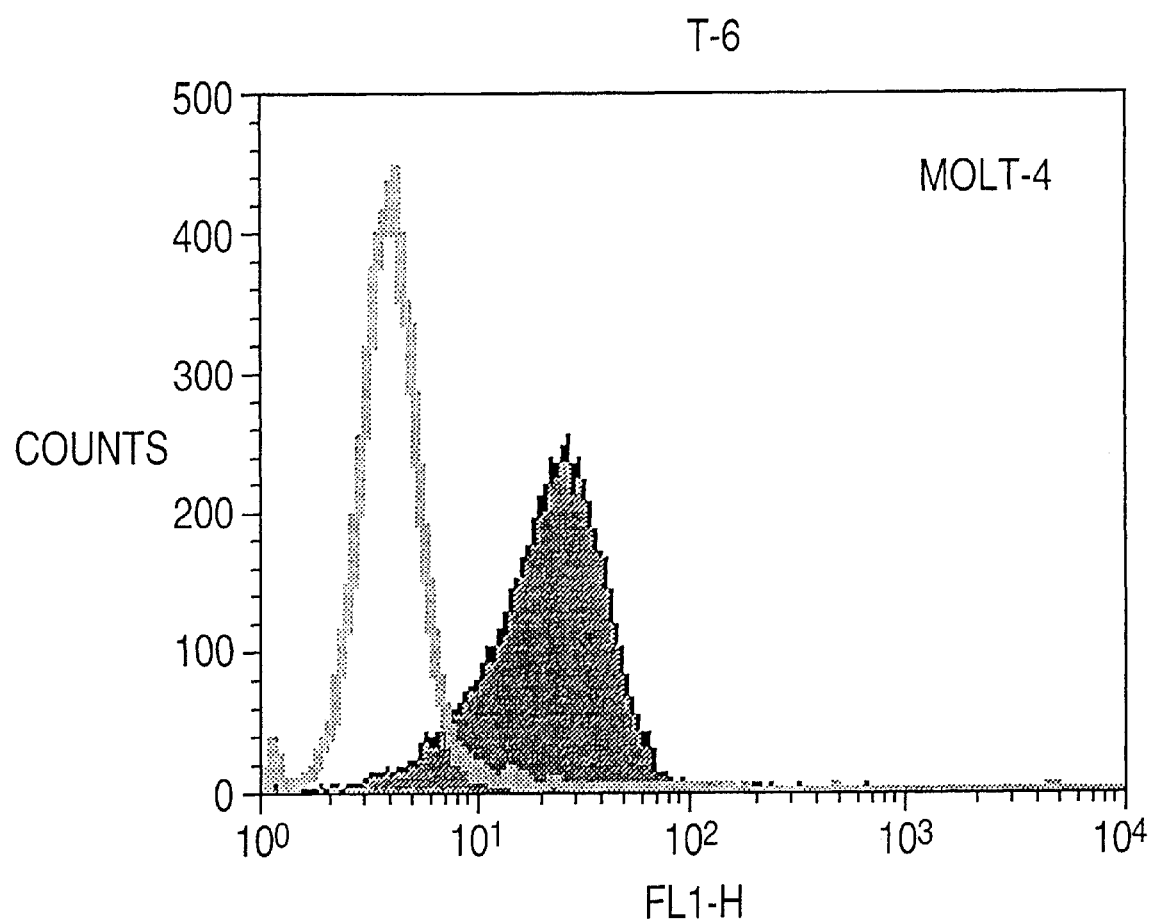
Figure 16:
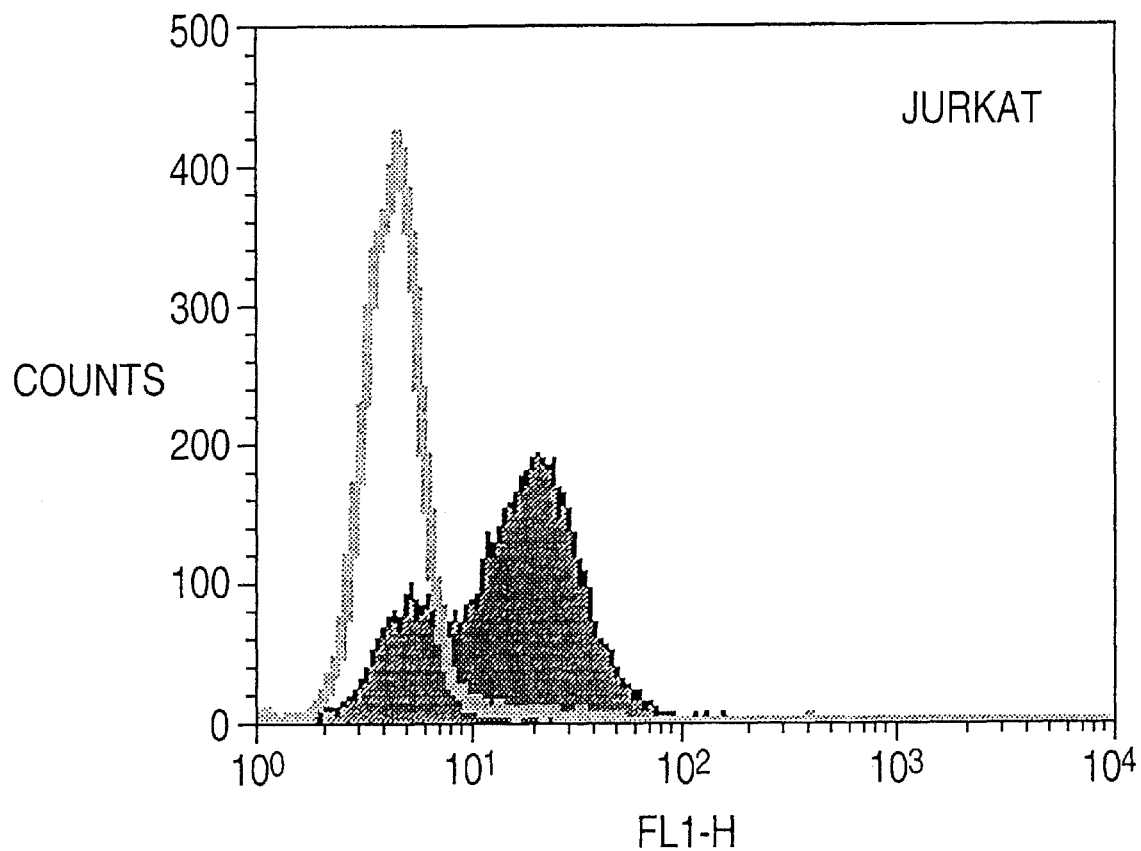
Figure 17:
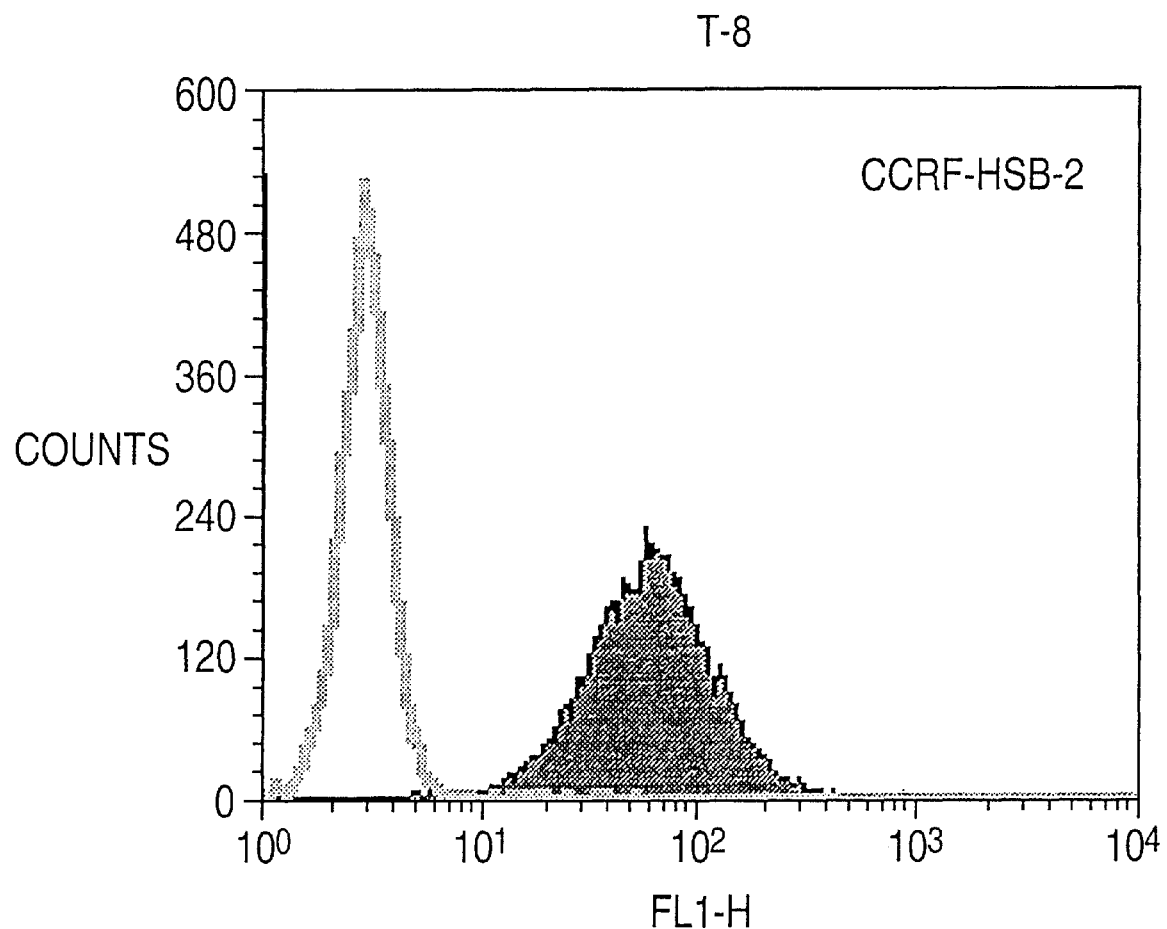
Figure 18:
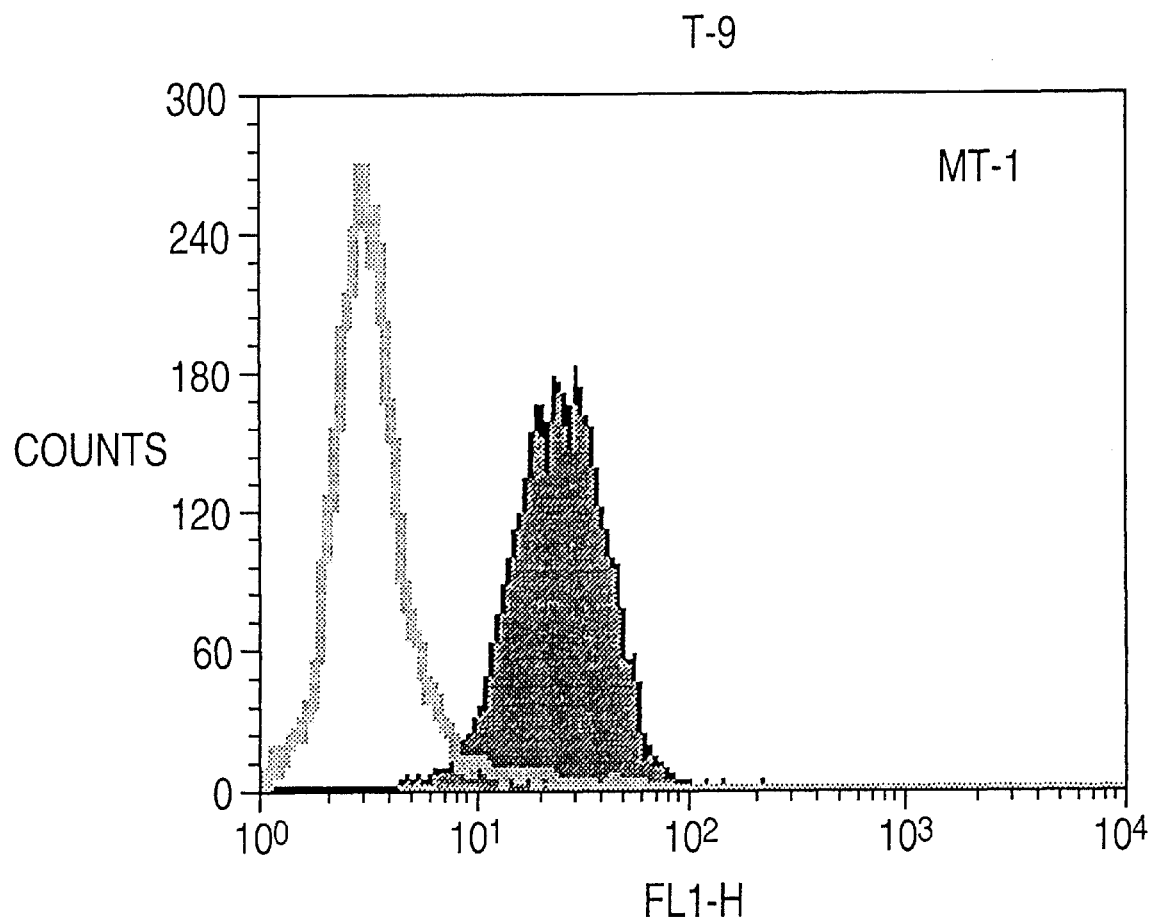
Figure 19:
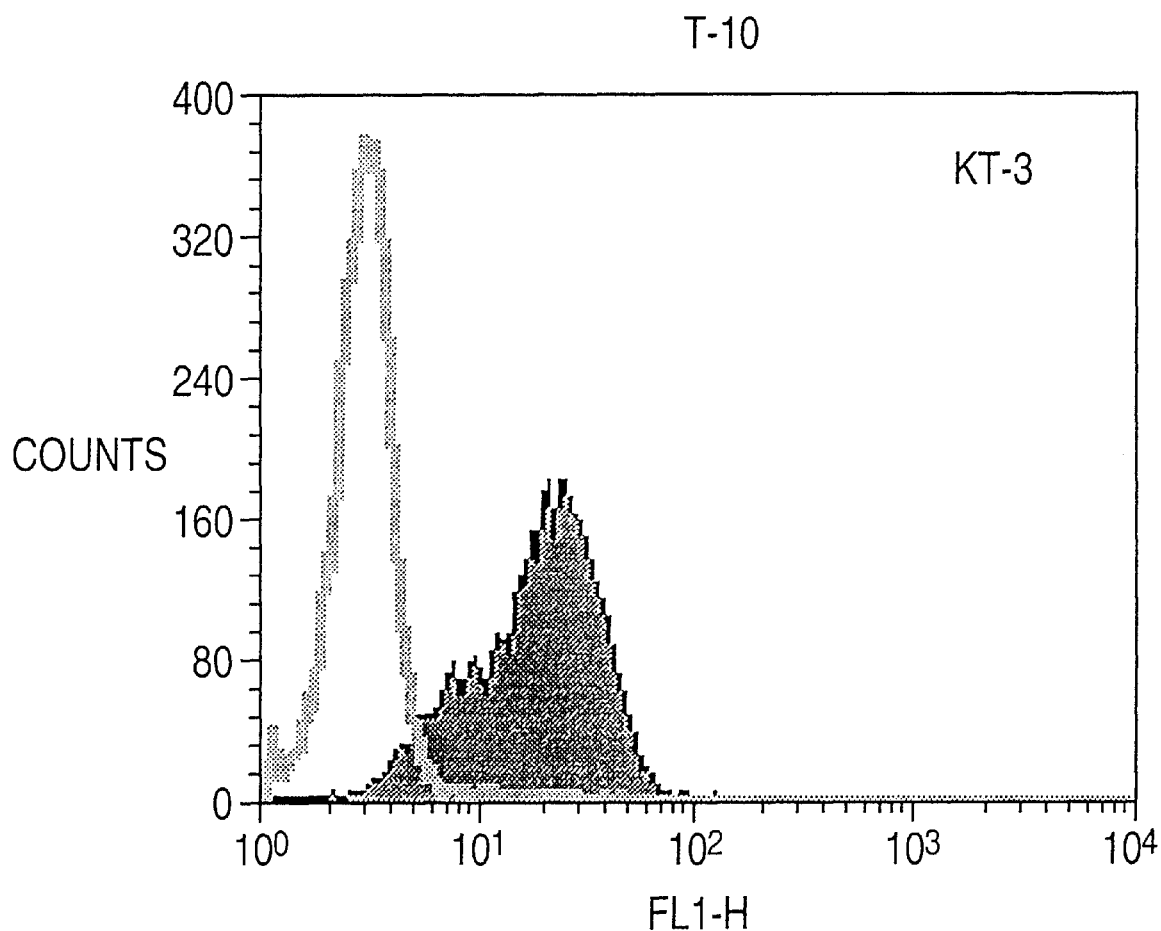
Figure 20:
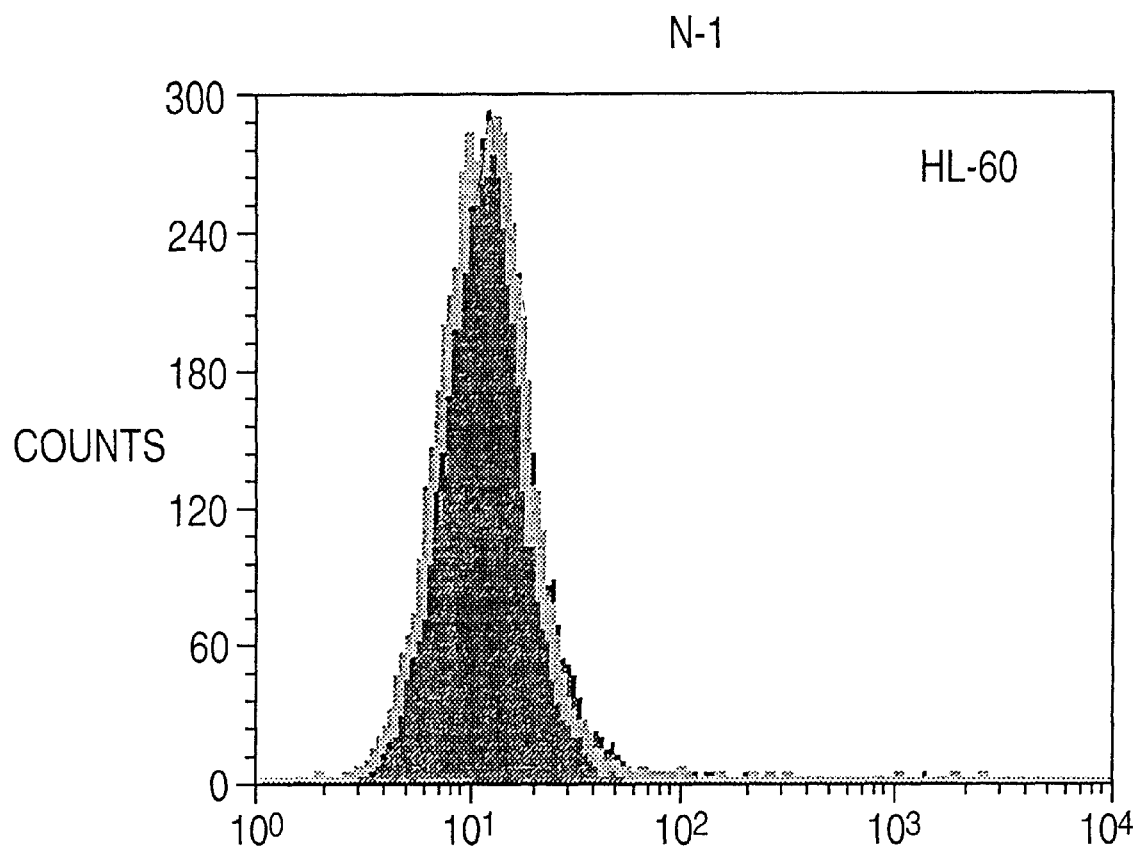
Figure 21:
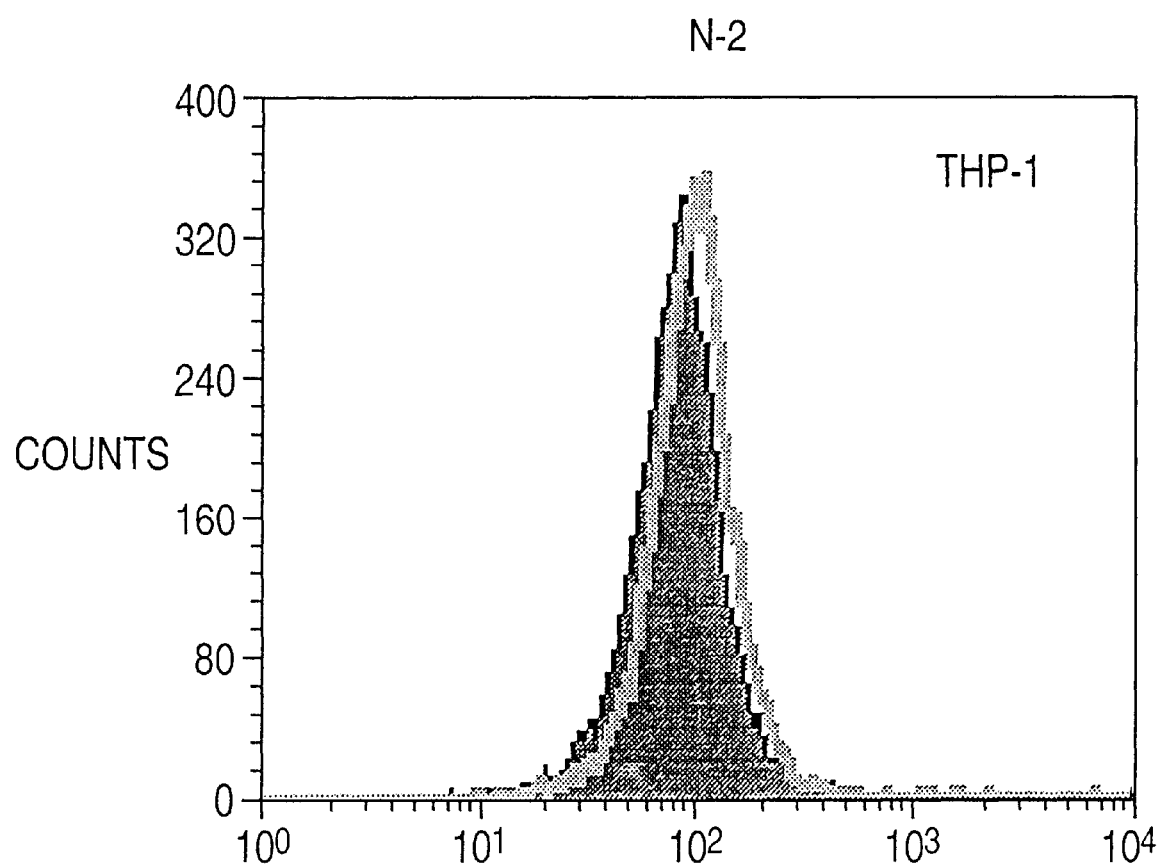
Figure 22:
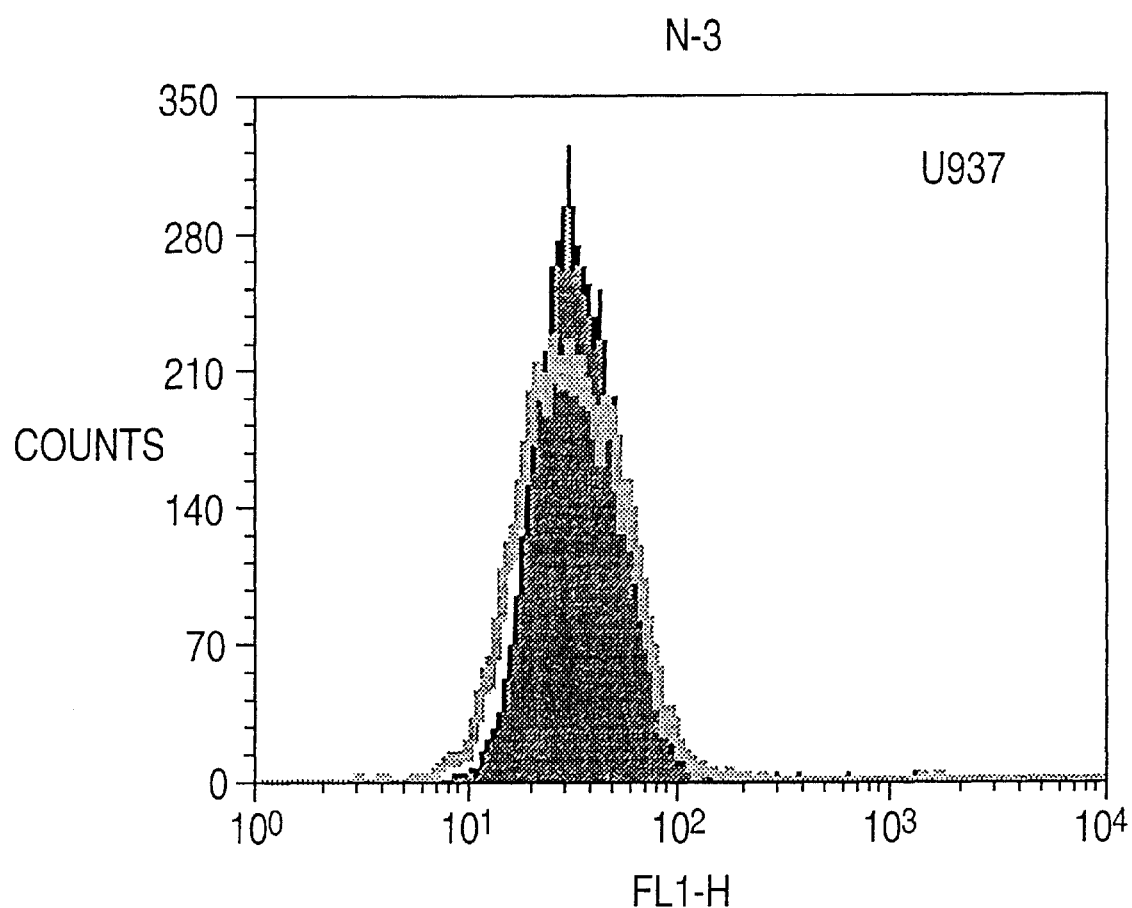
Figure 23:
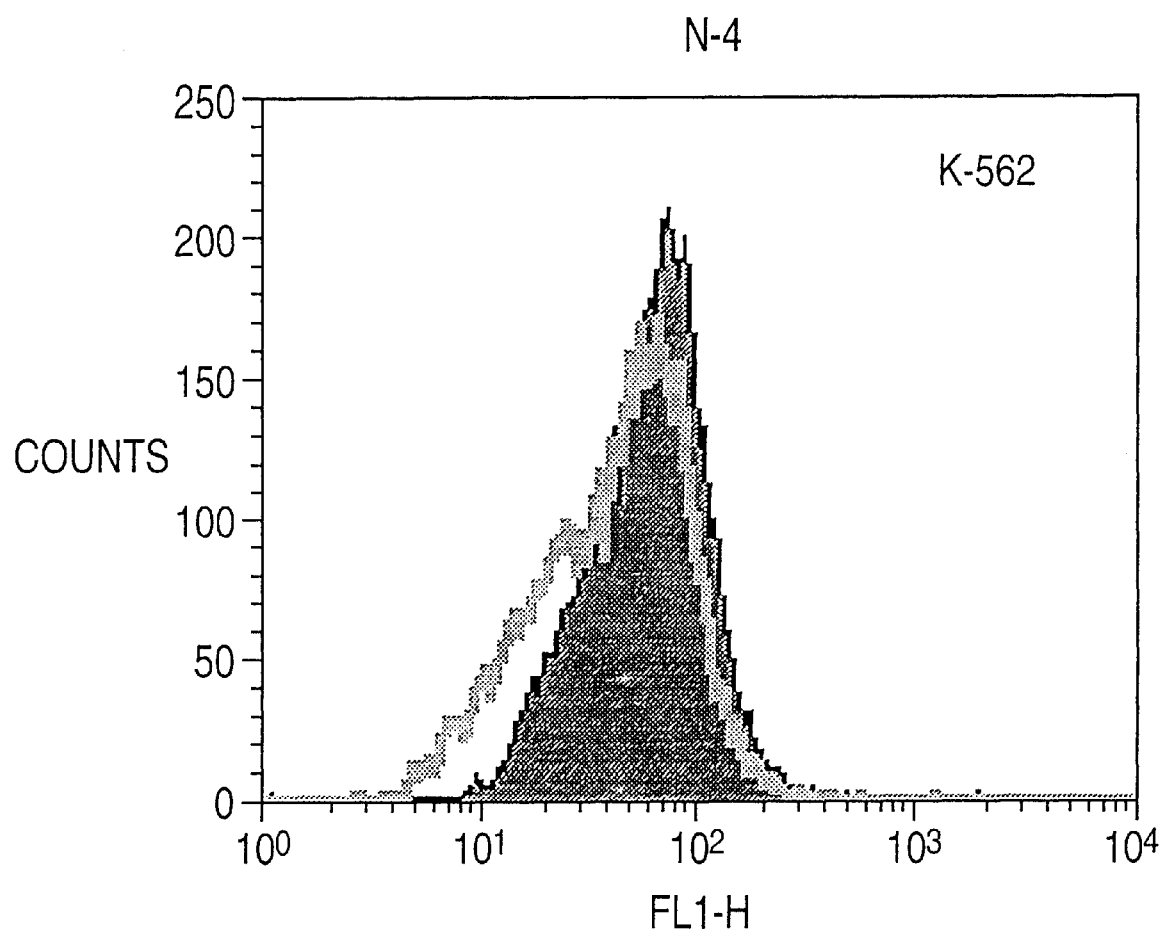

Hybridomas that produce antibodies for use in the present invention can be basically constructed using a known procedure as described below. Thus, HM1.24 antigen protein or cells that express HM1.24 antigen may be used as a sensitizing antigen and is used for immunization in the conventional method of immunization. The immune cells thus obtained are fused with known parent cells in the conventional cell fusion process, and then screened by the conventional screening method to select cells that produce monoclonal antibodies.

Specifically, monoclonal antibodies may be obtained in the following manner. For example, as a HM1.24 antigen-expressing cell which is a sensitizing antigen for obtaining antibody, there can be used a human multiple myeloma cell line KPMM2 (Japanese Unexamined Patent Publication (Kokai) No. 7-236475) or KPC-32 (Goto T. et al., Jpn. J. Clin. Hematol. (1991) 32, 1400). Alternatively, as a sensitizing antigen, there may be used a protein having the amino acid sequence as set forth in SEQ ID NO: 1 or a peptide or polypeptide containing an epitope recognized by anti-HM1.24 antibody.

As used herein, cDNA that encodes a protein having the amino acid sequence as set forth in SEQ ID NO: 1 has been inserted in the XbaI cleavage site of pUC19 vector to construct plasmid pRS38-pUC19. *E. coli* having this plasmid has been internationally deposited under the provisions of the Budapest Treaty as *Escherichia coli* DH5α (pRS38-pUC19) on Oct. 5, 1993 with the National Institute of Bioscience and Human-Technology, Agency of Industrial Science and Technology, of 1–3, Higashi 1-chome, Tsukuba city, Ibaraki pref., Japan, as FERM BP-4434 (see Japanese Unexamined Patent Publication (Kokai) No. 7-196694). The cDNA fragment contained in this plasmid pRS38-pUC19 can be used to prepare a peptide or a polypeptide containing an epitope recognized by anti-HM1.24 antibody by a genetic engineering technology.

Preferably mammals to be immunized with the sensitizing antigen are selected in consideration of their compatibility with the parent cell for use in cell fusion. They generally include, but not limited to, rodents such as mice, rats, hamsters and the like.

Immunization of animals with a sensitizing antigen is carried out using a known method. A general method, for example, involves the intraperitoneal or subcutaneous administration of a sensitizing antigen to mammal. Specifically, a sensitizing antigen which has been diluted and suspended in an appropriate amount of phosphate buffered saline (PBS) or physiological saline etc. is mixed, as desired, with an appropriate amount of Freund's complete adjuvant. After being emulsified, it is preferably administered to a mammal for several times every 4 to 21 days. Alternatively a suitable carrier may be used at the time of immunization with the sensitizing antigen.

After immunization and the confirmation of an increase in the desired antibody level in the serum, the immune cells are taken out from the mammal and are subjected to cell fusion, in which preferred immune cells include in particular the spleen cells.

The mammalian myeloma cells as the other parent cells which are subjected to cell fusion with the above-mentioned immune cells preferably include various known cell lines such as P3X63Ag8.653) (J. Immunol. (1979) 123:1548–1550), P3X63Ag8U.1 (Current Topics in Microbiology and Immunology (1978) 81:1–7), NS-1 (Kohler, G. and Milstein, C., Eur. J. Immunol. (1976) 6: 511–519), MPC-11 (Margulies, D. H. et al., Cell (1976) 8: 405–415), SP2/0 (Shulman, M. et al., Nature (1978) 276: 269–270), FO (de St. Groth, S. F. et al., J. Immunol. Methods (1980) 35:1–21), S194 (Trowbridge, I. S., J. Exp. Med. (1978) 148:313–323), R210 (Galfre, G. et al., Nature (1979) 277:131–133) and the like.

Cell fusion between the above immune cells and the myeloma cells may be essentially conducted in accordance with a known method such as is described in Milstein et al. (Kohler, G. and Milstein, C., Methods Enzymol. (1981) 73:3–46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are thoroughly mixed in the above culture medium, to which a PEG solution previously heated to about 37° C., for example a PEG solution with a mean molecular weight of about 1000 to 6000, is added at a concentration of 30 to 60% (w/v) and mixed to obtain desired fusion cells (hybridomas). Then, by repeating the sequential addition of a suitable culture medium and centrifugation to remove the supernatant, cell fusion agents etc. which are undesirable for the growth of the hybridoma can be removed.

Said hybridoma is selected by culturing in a conventional selection medium, for example, HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. The conventional limiting dilution method is conducted in which the hybridomas that produce the desired antibody are selected and monoclonally cloned.

In addition to obtaining the above hybridoma by immunizing an animal other than the human with an antigen, it is also possible to sensitize human lymphocytes in vitro with HM1.24 antigen or HM1.24 antigen-expressing cells, and the resulting sensitized lymphocytes are fused with human myeloma cells for example U266, to obtain the desired human antibody having the activity of binding to HM1.24 antigen or HM1.24 antigen-expressing cells (see Japanese Post-examined Patent Publication (Kokoku) No. 1-59878). Furthermore, a transgenic animal having a repertoire of all human antibody genes is immunized with the antigen, i.e., HM1.24 antigen or HM1.24 antigen-expressing cells, to obtain the desired humanized antibody in the method described above (see International Patent Applications WO 93/12227, WO 92/03918, WO 94/02602, WO 94/25585, WO 96/34096 and WO 96/33735).

The monoclonal antibody-producing hybridomas thus constructed can be subcultured in a conventional culture medium, or can be stored for a prolonged period of time in liquid nitrogen.

In order to obtain the monoclonal antibody from said hybridoma, there can be mentioned a method in which said hybridoma is cultured in a conventional method and the antibodies are obtained in supernatant, or a method in which the hybridoma is administered to and grown in a mammal compatible with said hybridoma and the antibodies are obtained in the ascites. The former method is suitable for obtaining high-purity antibodies, whereas the latter is suitable for a large scale production of antibodies.

Specifically the anti-HM1.24 antibody-producing hybridoma can be constructed using: the method of Goto, T. et al. (Blood (1994) 84:1922–1930). It can be conducted by a method in which the anti-HM1.24 antibody-producing hybridoma that was internationally deposited under the provisions of the Budapest Treaty as FERM BP-5233 on Sep. 14, 1995 with the National Institute of Bioscience and Human-Technology, Agency of Industrial Science and Technology, of 1–3, Higashi 1-chome, Tsukuba city, Ibaraki pref., Japan, is intraperitoneally injected to BALB/c mice (manufactured by CLEA Japan) to obtain the ascites from which the anti-HM1.24 antibody is purified, or: a method in which said hybridoma is cultured in a suitable culture medium such as the RPMI1640 medium containing 10% fetal bovine serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the anti-HM1.24 antibody can be purified from the supernatant.

1-2. Recombinant antibody

A recombinant antibody which was produced by the recombinant gene technology in which an antibody gene was cloned from the hybridoma and integrated into a suitable vector which was then introduced into a host can be used in the present invention as monoclonal antibody (see, for example, Carl, A. K., Borrebaeck, and James, W. Larrick, THERAPEUTIC MONOCLONAL ANTIBODIES, published in the United Kingdom by MACMILLAN PUBLISHERS LTD. 1990).

Specifically, mRNA encoding the variable region (V region) of the desired antibody is isolated from the hybridoma producing the antibody. The isolation of mRNA is conducted by preparing total RNA using, for example, a known method such as the guanidine ultracentrifuge method (Chirgwin, J. M. et al., Biochemistry (1979) 18, 5294–5299), the AGPC method (Chomczynski, P. et al., Analytical Biochemistry (1987) 162, 156–159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998–9002; Belyavsky, A. et al., Nucleic Acids Res. (1989) 17, 2919–2932) that employs polymerase chain reaction (PCR) may be used. The desired DNA fragment is purified from the PCR product obtained and may be ligated to vector DNA. Moreover, a recombinant vector is constructed therefrom and then is introduced into *E. coli* etc., from which colonies are selected to prepare a desired recombinant vector. The nucleotide sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

1-3. Altered antibody

In accordance with the present invention, artificially altered recombinant antibody such as chimeric antibody and humanized antibody can be used for the purpose of lowering heterologous antigenicity against humans. These altered antibodies can be produced using known methods.

Chimeric antibody can be obtained by ligating the thus obtained DNA encoding a V region of antibody to DNA encoding a C region of human antibody, which is then inserted into an expression vector and introduced into a host for production of the antibody therein (see European Patent Application EP 125023, and International Patent Application WO 96/02576). Using this known method, chimeric antibody useful for the present invention can be obtained.

For example, *E. coli* having the plasmid that contains DNA encoding an L chain V region or an H chain V region of chimeric anti-HM1.24 antibody has been internationally deposited under the provisions of the Budapest Treaty as *Escherichia coli* DH5α (pUC19-1.24L-gκ) and *Escherichia coli* DH5α (pUC19-1.24H-gγ1), respectively, on Aug. 29, 1996 with the National Institute of Bioscience and Human-Technology, Agency of Industrial Science and Technology, of 1–3, Higashi 1-chome, Tsukuba city, Ibaraki pref., Japan, as FERM BP-5646 and FERM BP-5644, respectively (see Japanese Patent Application No. 9-271536).

Humanized antibody which is also called reshaped human antibody has been made by grafting the complementarity determining region (CDR) of an antibody of a mammal other than the human, for example mouse antibody, into the CDR of human antibody. The general recombinant DNA technology for preparation of such antibodies is also known (see European Patent Application EP 125023 and International Patent Application WO 96/02576).

Specifically, a DNA sequence which was designed to ligate the CDR of mouse antibody with the framework region (FR) of human antibody is synthesized by PCR method from several divided oligonucleotides having sections overlapping with one another at the ends thereof. The DNA thus obtained is ligated to the DNA encoding the C region of human antibody and then is inserted into an expression vector, which is then introduced into a host for antibody production (see European Patent Application EP 239400 and International Patent Application WO 96/02576).

FRs of human antibody linked through CDRs are selected so that the complementarity determining regions form a favorable antigen binding site. When desired, amino acids in the framework regions of the antibody variable region may be substituted so that the complementarity determining region of reshaped human antibody may form an appropriate antigen biding site (Sato, K. et al., Cancer Res. (1993) 53, 851–856).

For example, *E. coli* having plasmid that contains a DNA encoding the version<u>a</u> (SEQ ID NO:2) of the L chain V region and that for the version<u>r</u> (SEQ ID NO:3) of the H chain V region of humanized anti-HM1.24 antibody has been internationally deposited under the provisions of the Budapest Treaty as *Escherichia coli* DH5α (pUC19-RVLa-AHM-gκ) and *Escherichia coli* DH5α (pUC19-RVHr-AHM-gγ1), respectively, on Aug. 29, 1996 with the National Institute of Bioscience and Human-Technology, Agency of Industrial Science and Technology, of 1–3, Higashi 1-chome, Tsukuba city, Ibaraki pref., Japan, as FERM BP-5645 and FERM BP-5643, respectively (Japanese Patent Application No. 9-271536). Furthermore, *E. coli* having plasmid containing a DNA encoding the version<u>s</u> (SEQ ID NO:4) of the H chain V region of humanized anti-HM1.24 antibody (SEQ ID NO:8) has been internationally deposited under the provisions of the Budapest Treaty as *Escherichia coli* DH5α (pUC19-RVHs-AHM-gγ1) on Sep. 29, 1997 with the National Institute of Bioscience and Human-Technology, Agency of Industrial Science and Technology, of 1–3, Higashi 1-chome, Tsukuba city, Ibaraki pref., Japan, as FERM BP-6127 (Japanese Patent Application No. 9-271536).

For chimeric antibody or humanized antibody, the C region of human antibody is used, and most preferably human Cγ such as Cγ1, Cγ2, Cγ3, and Cγ4 can be used as the constant region of human antibody. Among these, antibodies containing Cγ1 and Cγ3 have strong cytotoxic activity, i.e. ADCC activity and CDC activity, and hence are preferably used in the present invention.

Chimeric antibody comprises the variable region of antibody derived from a mammal other than the human and the C region derived from human antibody, whereas humanized antibody comprises the complementarity determining regions of an antibody derived from a mammal other than the human and the framework regions (FRs) and the C region of antibody derived from human antibody. Accordingly, antigenicity thereof in the human body has been reduced so that they are useful as the active ingredient of the therapeutic agents of the present invention.

A preferred embodiment of a humanized antibody for use in the present invention includes humanized anti-HM1.24 antibody (see Japanese Patent Application No. 9-271536). A preferred embodiment of an L chain V region of humanized anti-HM1.24 antibody includes one which has the amino acid sequence encoded by the nucleotide sequence (SEQ ID NO:6) as set forth in SEQ ID NO:2. A preferred embodiment of the H chain V region of humanized anti-HM1.24 antibody includes one which has the amino acid sequence (SEQ ID NOS:7 or 8) encoded by the base sequence as set forth in SEQ ID NO:3 or 4.

1-4. Expression and production

Antibody genes constructed as described above may be expressed and the antibody can be obtained in a known method. In the case of mammalian cells, expression may be accomplished using an expression vector containing a commonly used useful promoter, an antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when HEF1α promoter/enhancer is used.

In the case of *E. coli*, expression may be conducted by operably linking a commonly used useful promoter, a signal sequence for antibody secretion, and the antibody gene to be expressed, followed by expression thereof. As the promoter, for example, there can be mentioned lacz promoter and araB promoter. The method of Ward et al. (Nature (1989) 341, 544–546; FASEB J. (1992) 6, 2422–2427) may be used when lacz promoter is used, and the method of Better et al. (Science (1988) 240, 1041–1043) may be used when araB promoter is used.

As the signal sequence for antibody secretion, when produced in the periplasm of *E. coli*, the pelB signal sequence (Lei, S. P. et al., J. Bacteriol. (1987) 169, 4379) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, an expression vector can include as a selectable marker an aminoglycoside transferase (APH) gene, a thymidine kinase (TK) gene, an *E. coli* xanthine guaninephosphoribosyl transferase (Ecogpt) gene, a dihydrofolate reductase (dhfr) gene and the like.

For the production of antibody for use in the present invention, any production system can be used. The production system of antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as Xenopus oocytes, or (3) insect cells such as sf9, sf21, and Tn5. Known plant cells include, for example, those derived from the genus *Nicotiana*, more specifically cells derived from *Nicotiana tabacum*, which is subjected to callus culture. Known fungal cells include yeasts such as the genus *Saccharomyces*, more specifically *Saccharomyces cereviceae*, or filamentous fungi such as the genus *Aspergillus*, more specifically *Aspergillus niger*.

When the prokaryotic cells are used, there are the production systems which employ bacterial cells. Known bacterial cells include *Escherichia coli* (*E. coli*), and *Bacillus subtilis*.

By introducing via transformation the gene of the desired antibody into these cells and culturing the transformed cells in vitro, the antibody can be obtained. Culturing is conducted in the known methods. For example, as the culture media, DMEM, MEM, RPMI1640, and IMDM can be used, and serum supplements such as fetal calf serum (FCS) may be used in combination. In addition, antibodies may be produced in vivo by implanting cells, into which the antibody gene has been introduced, into the abdominal cavity of an animal and the like.

As further in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also as insects, silkworms can be used. When plants are used, tabacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or the offspring thereof. In order to increase the amount of milk containing the desired antibody produced by the transgenic goat, hormones may be given to the transgenic goat as appropriate. (Ebert, K. M. et al., Bio/Technology (1994) 12, 699–702).

When silkworms are used, baculovirus, into which a desired antibody gene has been inserted, is infected to the silkworm, and the desired antibody can be obtained from the body fluid of the silkworm (Susumu, M. et al., Nature (1985) 315, 592–594). Moreover, when tabacco is used, a desired antibody gene is inserted into an expression vector for plants, for example pMON 530, and then the vector is introduced into a bacterium such as *Agrobacterium tumefaciens*. The bacterium is then infected to tabacco such as *Nicotiana tabacum* to obtain the desired antibody from the leaves of the tabacco (Julian, K. -C. Ma et al., Eur. J. Immunol. (1994) 24, 131–138).

When antibody is produced in vitro or in vivo production systems, as described above, DNA encoding the heavy chain (H chain) or the light chain (L chain) of antibody may be separately inserted into an expression vector and the hosts are transformed simultaneously, or DNA encoding the H chain and the L chain may be integrated into a single expression vector and the host is transformed therewith (see International Patent Application WO 94-11523).

The antibody produced as described above can be bound to various molecules such as polyethylene glycol (PEG) for use as a modified antibody. "Antibody" as used herein includes these modified antibodies. In order to obtain such a modified antibody, the antibody obtained may be chemically modified. These methods have already been established in the field of the art.

2. Separation and Purification of Antibody 2-1. Separation and purification of antibody Antibodies produced and expressed as described above can be separated from the inside or outside of the cell or from the host and then may be purified to homogeneity. Separation and purification of the antibody for use in the present invention may be accomplished by affinity chromatography. As the column used for such affinity chromatography, there can be mentioned Protein A column and Protein G column. Examples of the carriers for Protein A column are Hyper D, POROS, Sepharose F. F. and the like.

Alternatively, methods for separation and purification conventionally used for proteins can be used without any limitation. Separation and purification of an antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into HPLC. Alternatively, reverse-phase chromatography can be used.

2-2. Determination of antibody concentration

The concentration of antibody obtained in the above 2-1 can be determined by the measurement of absorbance or by the enzyme-linked immunosorbent assay (ELISA) and the like. Thus, when absorbance measurement is employed, the antibody for use in the present invention or a sample containing the antibody is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 μl of goat anti-human IgG (manufactured by BIO SOURCE) diluted to 1 μg/ml in 0.1 M bicarbonate buffer, pH 9.6, is added to a 96-well plate (manufactured by Nunc), and is incubated overnight at 4° C. to immobilize the antibody.

After blocking, 100 μl each of appropriately diluted antibody of the present invention or a sample containing the antibody, or 100 μl of human IgG of a known concentration as the standard is added, and incubated at room temperature for 1 hour. After washing, 100 μl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

3. FCM Analysis

Reactivity of the antibody for use in the present invention with lymphatic tumor cells may be investigated by the flow cytometry (FCM) analysis. The cells used may be established cell lines or freshly isolated cells. As the established cell lines, there can be used, for example, as a T cell line RPMI 8402 (ATCC CRL-1994), CCRF-CEM (ATCC CCL-119) derived from acute lymphoblastic leukemia, HPB-ALL (FCCH1018) derived from acute lymphatic leukemia, HPB-MLT (FCCH1019) derived from T lymphoma, JM (FCCH1023) derived from acute lymphatic leukemia, MOLT-4 (ATCC CRL-1582) derived from acute lymphoblastic leukemia, Jurkat (FCCH1024) derived from acute lymphatic leukemia, CCRF-HSB-2 (ATCC CCL-120.1) derived from acute lymphoblastic leukemia, MT-1 (FCCH1043) derived from adult T cell leukemia, KT-3 derived from Lennert's lymphoma (Shimizu, S. et al., Blood (1988) 71, 196–203) and the like; as the B cell line an EB virus-transformed cell CESS (ATCC TIB-190), an EB virus positive B cell SKW 6.4 (ATCC TIB-215), MC116 (ATCC CRL-1649) derived from B lymphoma, CCRF-SB (ATCC CCL-120) derived from acute lymphoblastic leukemia, B cell RPMI 6410 (FCCH6047) derived from a patient with acute myelocytic leukemia, Daudi (ATCC CCL-213) derived from Burkitt lymphoma, EB-3 (ATCC CCL-85) derived from Burkitt lymphoma, Jijoye (ATCC CCL-87) derived from Burkitt lymphoma, Raji (ATCC CCL-86) derived from Burkitt lymphoma, and; as the non-T, non-B cell line HL-60 (ATCC CCL-240) derived from acute myelocytic leukemia, THP-1 (ATCC TIB-202) derived from acute monocytic leukemia, U-937 (ATCC CRL-1593) derived from histiocytic lymphoma, K-562 (ATCC CCL-243) derived from chronic myelocytic leukemia and the like.

After washing the above cells in PBS(−), 100 μl of an antibody or a control antibody diluted to 25 μg/ml in the FACS buffer (PBS(−) containing 2% fetal bovine serum and 0.1% sodium azide) is added thereto, which is then incubated on ice for 30 minutes. After washing in the FACS buffer, 100 μl of 25 μg/ml FITC-labeled goat anti-mouse antibody (GAM, manufactured by Becton Dickinson) is added thereto, which is then incubated on ice for 30 minutes. After washing in the FACS buffer, the cells are suspended in 600 μl or 1 ml of the FACS buffer, and each of the cells may be measured for its fluorescence intensity using the FACScan (manufactured by Becton Dickinson).

From the measured value of fluorescence intensity for each of the cells, the reactivity of the antibody for use in the present invention with each of the cells can be known. Thus, from the measured value of fluorescence intensity for each of the cells, it can be known whether HM1.24 antigen is expressed on each of the cells (positive or negative) or the degree of expression can be known. The presence and the intensity of expression of HM1.24 antigen in lymphatic tumor cells are described in Example 2. 2. FCM analysis below.

The tumor cells of lymphatic tumors that may be the target of treatment of the present invention are expressing HM1.24 antigen. More specifically, the tumor cells of lymphatic tumors are preferably those in which the positivity percentage of HM1.24 antigen is not lower than 5%. More specifically, the tumor cells of lymphatic tumors are preferably those in which the positivity percentage of HM1.24 antigen is 20% or higher. More specifically, the tumor cells of lymphatic tumors are preferably those in which the positivity percentage of HM1.24 antigen is 50% or higher. More specifically, the tumor cells of lymphatic tumors are preferably those in which the positivity percentage of HM1.24 antigen is 80% or higher.

4. Cytotoxic Activity

4-1. Measurement of the CDC activity

The antibody for use in the present invention is one which has, for example, a CDC activity as the cytotoxic activity.

The CDC activity of a therapeutic agent for lymphatic tumors of the present invention can be measured in the following manner. First, the target cells are prepared at $4 \times 10^5$ cells/ml in a suitable medium, for example an RPMI1640 medium containing 10% fetal bovine serum (manufactured by GIBCO-BRL). As the target cells, there can be used CCRF-CEM (ATCC CCL-119), CCRF-HSB-2 (ATCC CCL-120.1), HPB-MLT (FCCH1019), EB-3 (ATCC CCL-85), MC116 (ATCC CRL-1649), CCRF-SB (ATCC CCL-120), K-562 (ATCC CCL-243) and the like. Fifty $\mu$l of these cells is added to a 96-well flat-bottomed plate (manufactured by FALCON) and the plate is incubated in a $CO_2$ incubator at 37° C. overnight.

Then the antibody for which the CDC activity is to be measured is added and incubated for 60 minutes, and then appropriately diluted complement, for example Baby Rabbit Complement (manufactured by CEDARLANE) is added thereto and incubated for 2 hours. To each of the wells is added 10 $\mu$l of Alamar Bule (manufactured by BIO SOURCE) and incubated for 4 hours, which is then measured for its fluorescence intensity (excitation wavelength 530 nm, emission wavelength 590 nm) using a fluorescence measurement system CytoFluor 2350 (manufactured by MILLIPORE). The cytotoxic activity (%) can be calculated as $(A-C)/(B-C) \times 100$, in which A is a fluorescence intensity when incubated in the presence of the antibody, B is a fluorescence intensity when incubated in the medium alone containing no antibody, and C is a fluorescence intensity of the well containing no cells.

4-2. Measurement of the ADCC activity

The antibody for use in the present invention is one which has, for example, an ADCC activity as the cytotoxic activity.

The ADCC activity of a therapeutic agent for lymphatic tumors of the present invention can be measured in the following manner. First, mononuclear cells are isolated as the effector cells from human peripheral blood or bone marrow by the gravity centrifuge method. As the target cells, CCRF-CEM (ATCC CCL-119), CCRF-HSB-2 (ATCC CCL-120.1), HPB-MLT (FCCH1019), EB-3 (ATCC CCL-85), MC116 (ATCC CRL-1649), CCRF-SB (ATCC CCL-120), K-562 (ATCC CCL-243) or the like are labeled with $^{51}Cr$ to be prepared as the target cells. Subsequently, to the labeled target cells is added the antibody to be measured for the ADCC activity and incubated. Effector cells at a suitable ratio to the target cells are then added and incubated.

After the incubation the supernatant is collected and measured for radioactivity using a gamma counter, whereupon 1% NP-40 can be used for measurement of a maximum free radioactivity. The cytotoxic activity (%) can be calculated as $(A-C)/(B-C) \times 100$, in which A is radioactivity (cpm) liberated in the presence of the antibody, B is radioactivity (cpm) liberated by NP-40, and C is radioactivity (cpm) liberated by the medium alone containing no antibody.

4-3. Enhancement of cytotoxic activity

In order to exhibit a cytotoxic activity such as an ADCC activity and a CDC activity, it is preferred to use C$\gamma$, in particular C$\gamma$1 and C$\gamma$3 as the constant region (C region) of antibody in humans. Furthermore, a stronger ADCC activity or CDC activity can be induced by adding, altering, or modifying part of the amino acids in the C region of antibody.

By way of example, there can be mentioned the construction of an IgM-like polymer of IgG by amino acid substitution (Smith, R. I. F. & Morrison, S. L. BIO/TECHNOLOGY (1994) 12, 683–688), the construction of an IgM-like polymer of IgG by amino acid addition (Smith, R. I. F. et al., J. Immunology (1995) 154, 2226–2236), the expression of a tandemly-ligated gene encoding L chain (Shuford, W. et al., Science (1991) 252, 724–727), the dimerization of IgG by amino acid substitution (Caron, P. C. et al., J. Exp. Med. (1992) 176, 1191–1195, Shopes, B., J. Immunology (1992) 148, 2918–2922), the dimerization of IgG by chemical modification (Wolff, E. A. et al., Cancer Res. (1993) 53, 2560–2565), and the introduction of the effector function by altering an amino acid(s) in the hinge region of antibody (Norderhaug, L. et al., Eur. J. Immunol. (1991) 21, 2379–2384) and the like. These can be accomplished by means of the oligomer site-specific mutagenesis using a primer, the addition of a base sequence using a restriction enzyme cleavage site, the use of a chemical modifier that creates a covalent bond.

5. Confirmation of Therapeutic Effects

The therapeutic effects of a therapeutic agent for use in the present invention for lymphatic tumors can be confirmed by administering the antibody for use in the gopresent invention to animals that have been transplanted with lymphatic tumor cells and then by evaluating the antitumor effect on the animals.

As lymphatic tumor cells to be given to the animal, there can be used an established cell line or freshly isolated cells. As the established cell line, there can be used CCRF-CEM (ATCC CCL-119), HPB-MLT (FCCH1019), MOLT-4 (ATCC CRL-1582), CCRF-HSB-2 (ATCC CCL-120.1) and the like as the T cell line, and CESS (ATCC TIB-190), SKW 6.4 (ATCC TIB-215), CCRF-SB (ATCC CCL-120), RPMI 6410 (FCCH6047), EB-3 (ATCC CCL-85) and the like as the B cell line.

Animals that receive transplantation are preferably those in which immunological functions are reduced or absent. For example, there can be used a nude mouse, a SCID mouse, a beige mouse, a nude rat and the like. The antitumor effects to be evaluated can be confirmed by the measurement of volume and weight of tumor, or the survival period of the animals and the like.

As shown in Examples below, the administration of anti-HM1.24 antibody resulted in the suppression of an increase in tumor volume and furthermore the extension of the survival period of the tumor-transplanted mice. These facts indicated that anti-HM1.24 antibody has an antitumor effect on lymphatic tumors.

6. Route of Administration and Pharmaceutical Preparation

The therapeutic agents for lymphatic tumors of the present invention may be administered, either systemically or locally, by a parenteral route, for example intravenous injection such as drip infusion, intramuscular injection, intraperitoneal injection, and subcutaneous injection. The method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

The therapeutic agents for lymphatic tumors of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof depending on the dosage form.

The diseases to be treated according to the present invention are lymphatic tumors (excluding myeloma) that have an antigen on the tumor cells, to which the antibody for use in the present invention binds. Specifically there may be mentioned acute B lymphatic leukemia (B-ALL), chronic B lymphatic leukemia (B-CLL), pre-B lymphoma, Burkitt lymphoma, follicular lymphoma, follicular pallium lymphoma, diffuse lymphoma, acute T lymphatic leukemia (T-ALL), chronic T lymphatic leukemia (T-CLL), adult T cell leukemia (ATL), non-ATL peripheral T lymphoma (PNTL) and the like. The therapeutic agents of the present invention are useful as therapeutic agents for these lymphatic tumors

EXAMPLES

The present invention will now be explained hereinbelow in more detail with reference to the following examples. It is to be noted that the present invention is not limited to these examples in any way.

Example 1

Construction of Anti-HM1.24 Antibody

1. Preparation of mouse ascites containing Anti-HM1.24 antibody

Hybridomas producing anti-HM1.24 antibody were obtained according to the method of Goto, T. et al. (Blood (1994) 84, 1922–1930).

To a BALB/c mouse (bred by CLEA Japan) that previously received intraperitoneal administration of 500 µl each of 2,6,10,14-tetramethyl pentadecane (manufactured by Wako Pure Chemical Industries, Ltd.) 11 and 3 days before, $5 \times 10^6$ hybridoma cells were intraperitoneally injected. From day 10 after the injection of hybridoma cells, the ascites that accumulated in the abdominal cavity of the mouse was collected via a 19-gauge indwelling needle Happycas (manufactured by Medikit). The collected ascites was centrifuged twice at a revolving speed of 1000 and 3000 rpm using a low-speed centrifuge RLX-131 (manufactured by Tomy Seiko) to remove the hybridoma and contaminants such as blood cells and the like.

2. Purification of anti-HM1.24 antibody from mouse ascites

Purification of anti-HM1.24 antibody from the above mouse ascites was conducted in the following method.

After adding an equal amount of PBS(−) to the mouse ascites, the mixture was filtered using a hollow fiber filter Mediaprep (manufactured by MILLIPORE) and then was affinity-purified using a high speed antibody purification instrument ConSep LC100 (manufactured by MILLIPORE) and the Hyper D Protein A column (column volume 20 ml, manufactured by Nihon Gaisi), and PBS(−) as the adsorption buffer and 0.1 M sodium citrate buffer (pH 4) as the elution buffer according to the attached instructions. The eluted fractions were immediately adjusted to about pH 7.4 by adding 1 M Tris-HCl (pH 8.0), and then were subjected to concentration and buffer replacement to PBS(−) using a centrifuge ultrafiltration concentrator Centriprep 10, which was then filter-sterilized with a membrane filter MILLEX-GV (manufactured by MILLIPORE) having a pore size of 0.22 µm to obtain the purified anti-HM1.24 antibody.

3. Determination of antibody concentration

The concentration of the purified antibody was determined by the measurement of absorbance. Thus, the purified antibody was diluted in PBS(−), the absorbance at 280 nm was measured, and the concentration was calculated using 1.35 OD at 1 mg/ml.

Example 2

A Study on the Reactivity of Anti-HM1.24 Antibody with Lymphatic Tumor Cells

1. Purification of control mouse IgG2a

Control mouse IgG2a was purified in the following method. Commercially available IgG2a (KAPPA) (UPC 10) ascites (manufactured by CAPPEL) was dissolved in purified water and PBS(−). The solution was filtered using a membrane filter Acrodisc (manufactured by Gelman Sciences) having a pore size of 0.2 µm, and then was affinity-purified using a high speed antibody purification instrument ConSep LC100 (manufactured by MILLIPORE) and the Hyper D Protein A column (column volume 20 ml, manufactured by Nihon Gaisi), and PBS(−) as the adsorption buffer and 0.1 M sodium citrate buffer (pH 4) as the elution buffer according to the attached instructions.

The eluted fractions were immediately adjusted to about pH 7.4 by adding 1 M Tris-HCl (pH 8.0), and then were subjected to concentration and buffer replacement to PBS(−) using a centrifuge ultrafiltration concentrator Centriprep 10, which was then filter-sterilized with a membrane filter MILLEX-GV (manufactured by MILLIPORE) having a pore size of 0.22 µm to obtain the purified control mouse IgG2a.

The determination of concentration of control mouse IgG2a was conducted according to the above 3. Determination of antibody concentration.

2. FCM analysis

Reactivity of the anti-HM1.24 antibody with lymphatic tumor cells was investigated by the flow cytometry (FCM) analysis. After washing a T cell line RPMI 8402 (ATCC CRL-1995), CCRF-CEM (ATCC CRL-119) derived from acute lymphoblastic leukemia, HPB-ALL (FCCH1018) derived from acute lymphatic leukemia, HPB-MLT (FCCH1019) derived from T lymphoma, JM (FCCH1023) derived from acute lymphatic leukemia, MOLT-4 (ATCC CRL-1582) derived from acute lymphoblastic leukemia, Jurkat (FCCH1024) derived from acute lymphatic leukemia, CCRF-HSB-2 (ATCC CCL-120.1) derived from acute lymphoblastic leukemia, MT-1 (FCCH1043) derived from adult T cell leukemia, and KT-3 derived from Lennert's lymphoma (Shimizu, S. et al., Blood (1988) 71, 196–203); as the B cell line an EB virus-transformed cell CESS (ATCC TIB-190), an EB virus positive B cell SKW 6.4 (ATCC TIB-215), MC116 (ATCC CRL-1649) derived from B lymphoma, CCRF-SB (ATCC CCL-120) derived from acute lymphoblastic leukemia, B cell RPMI 6410 (FCCH6047) derived from a patient with acute myelocytic leukemia, Daudi (ATCC CCL-213) derived from Burkitt lymphoma, EB-3 (ATCC CCL-85) derived from Burkitt lymphoma, Jijoye (ATCC CCL-87) derived from Burkitt lymphoma, Raji (ATCC CCL-86) derived from Burkitt lymphoma, and; as the non-T, non-B cell line HL-60 (ATCC CCL-240) derived from acute myelocytic leukemia, THP-1 (ATCC TIB-202) derived from acute monocytic leukemia, U-937 (ATCC CRL-1593) derived from histiocytic lymphoma, and K-562 (ATCC CCL-243) derived from chronic myelocytic leukemia in PBS(−), 100 µl of anti-HM1.24 antibody or a purified control mouse IgG2a antibody diluted to 25 µg/ml in the FACS buffer (PBS(−) containing 2% fetal bovine serum and 0.1% sodium azide) was added thereto, which was then incubated on ice for 30 minutes.

After washing in the FACS buffer, 100 µl of 25 µg/ml FITC-labeled goat anti-mouse antibody (GAM) was added thereto, which was then incubated on ice for 30 minutes. After washing in the FACS buffer, the cells were suspended in 600 µl or 1 ml of the FACS buffer, and each cell suspension was measured for its fluorescence intensity using the FACScan (manufactured by Becton Dickinson). The results, as shown in FIGS. 1–23, confirmed that all T cell lines and all B cell lines (except Daudi and Raji which did not react) reacted with anti-HM1.24 antibody and highly expressed HM1.24 antigen. On the other hand, none of the non-T, non-B cell lines reacted with anti-HM1.24 antibody and the expression of the antigen was not detected in any of them.

In the histograms in FIGS. 1 to 23, histogram markers were set up so that the negative cells account for 98% and the positive cells 2% in the staining with the control mouse IgG2a. Then, according to the histogram markers, the percentage of the HM1.24 antigen-positive cells when anti-HM1.24 antibody was used was calculated and the result is shown in Table 1. By the percentage of the HM1.24 antigen-positive cells, the expression rate of HM1.24 antigen was divided into 5 stages: −, +/−, +, ++, and +++. As a result, it was confirmed that all T cell lines and B cell lines (except Daudi and Raji) highly expressed HM1.24 antigen similarly to the results in FIGS. 1 to 23. Also, in all cases of the non-T, non-B cell lines the percentage of the HM1.24 antigen-positive cells was negative or less than 5%, indicating that the expression of the antigen is absent or very little.

TABLE 1

| | Name of cell | Expression rate | |
|---|---|---|---|
| B cell line | CESS | +++ | 94.5 |
| | SKW 6.4 | +++ | 92.8 |
| | MC116 | ++ | 65.0 |
| | CCRF-SB | +++ | 98.4 |
| | RPMI 6410 | +++ | 94.5 |
| | EB-3 | +++ | 88.3 |
| | Jijoye | +++ | 92.3 |
| | Daudi | − | 2.8 |
| | Raji | − | 2.0 |
| T cell line | RPMI 8402 | +++ | 94.0 |
| | CCRF-CEM | +++ | 97.8 |
| | HPB-ALL | ++ | 63.8 |
| | HPB-MLT | +++ | 94.6 |
| | JM | +++ | 99.6 |
| | MOLT-4 | +++ | 84.1 |
| | Jurkat | ++ | 70.9 |
| | CCRF-HSB-2 | +++ | 100.0 |
| | MT-1 | +++ | 95.9 |
| | KT-3 | +++ | 96.0 |

TABLE 1-continued

| | Name of cell | Expression rate | |
|---|---|---|---|
| Non-T, non-B cell line | HL-60 | − | 2.9 |
| | THP-1 | − | 1.5 |
| | U-937 | − | 1.1 |
| | K-562 | − | 3.9 |

−, <5%; +/−, 5–20%; +, 20–50%; ++, 50–80%; +++, >80%

Example 3

Determination of CDC Activity

The CDC activity of anti-HM1.24 antibody to lymphatic tumor cells was determined as follows:

1. Preparation of the target cells

As the target cell, CCRF-CEM (ATCC CCL-119) derived from acute lymphatic leukemia, CCRF-HSB-2 (ATCC CCL-120.1) derived from acute lymphoblastic leukemia, HPB-MLT (FCCH1019) derived from T lymphoma, EB-3 (ATCC CCL-85) derived from Burkitt lymphoma, MC 116 (ATCC CRL-1649) derived from Burkitt lymphoma, CCRF-SB (ATCC CCL-120) derived from acute lymphatic leukemia, and K562 (ATCC CCL-243) derived from chronic myelocytic leukemia were prepared at $4 \times 10^5$ cells/ml in an RPMI1640 medium (manufactured by GIBCO-BRL) containing 10% fetal bovine serum (GIBCO-BRL). Fifty µl each of these cell suspensions was added to a 96-well flat-bottomed plate (manufactured by FALCON) and incubated in a 5% $CO_2$ high-humidity incubator (manufactured by TABAI) at 37° C. overnight.

2. Preparation of anti-HM1.24 antibody

The purified anti-HM1.24 antibody obtained in the above Example 1 was prepared at 0, 0.2, 2, and 20 µg/ml in an RPMI1640 medium containing 10% fetal bovine serum (manufactured by GIBCO-BRL), and 50 µl of them was added to the 96-well flat-bottomed plate prepared in the above 1. After incubating the plate in a 5% $CO_2$ high-humidity incubator (manufactured by TABA1) at 37° C. for 60 minutes, it was centrifuged in a low speed centrifuge 05PR-22 (manufactured by Hitachi) at 1000 rpm for 5 minutes, and 50 µl of the supernatant was removed.

3. Preparation of complement

Baby Rabbit Complement (manufactured by CEDARLANE) was dissolved in purified water at 1 ml per vial, which was further diluted in 5 ml of an RPMI1640 medium (manufactured by GIBCO-BRL) containing no FCS. Fifty µl of this was dispensed to the 96-well flat-bottomed plate prepared in the above section 2 and was incubated in a 5% $CO_2$ high-humidity incubator (manufactured by TABA1) at 37° C. for 2 hours.

4. Determination of the CDC activity

After incubation was over, 10 µl of Alamar Blue (manufactured by BIO SOURCE) was added to each well of the 96-well flat-bottomed plate of the above section 3 and was incubated in a 5% $CO_2$ high-humidity incubator (manufactured by TABA1) at 37° C. for 4 hours. Each well was then measured for fluorescence intensity (excitation wavelength 530 nm, emission wavelength 590 nm) using a fluorescence measurement system CytoFluor 2350 (manufactured by MILLIPORE). The cytotoxic activity (%) was calculated as $(A-C)/(B-C) \times 100$, in which A is a fluorescence intensity when incubated in the presence of the antibody, B is a fluorescence intensity when incubated in the in the medium alone containing no antibody, and C is a fluorescence intensity of the well containing no cells.

Figure 24:
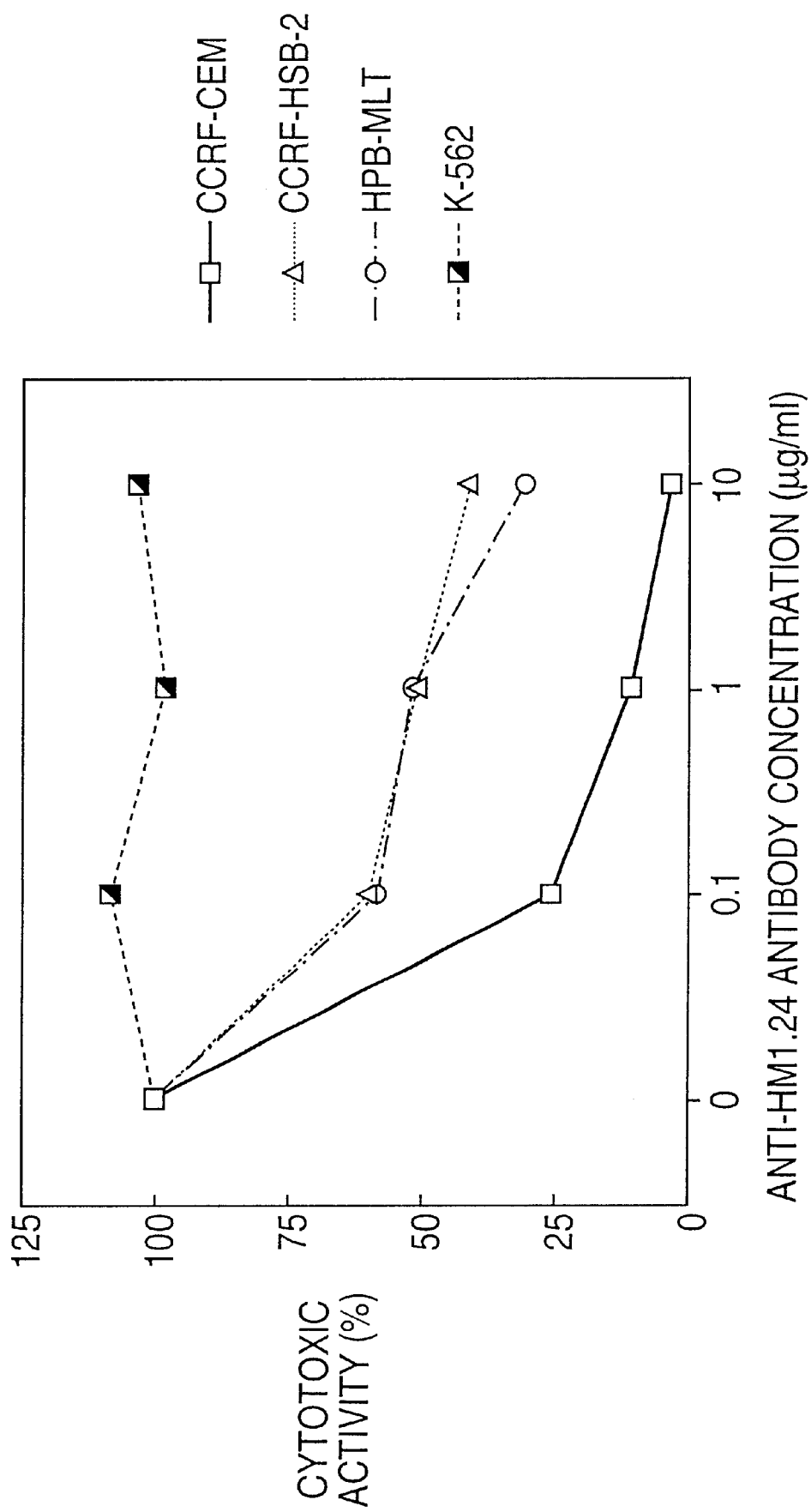
FIG. 24 is a graph showing that anti-HM1.24 antibody is exerting a cytotoxic effect on T cell tumor cell lines CCRF-CEM, CCRF-HSB-2, and HPB-MLT in a dose-dependent manner.
Figure 25:
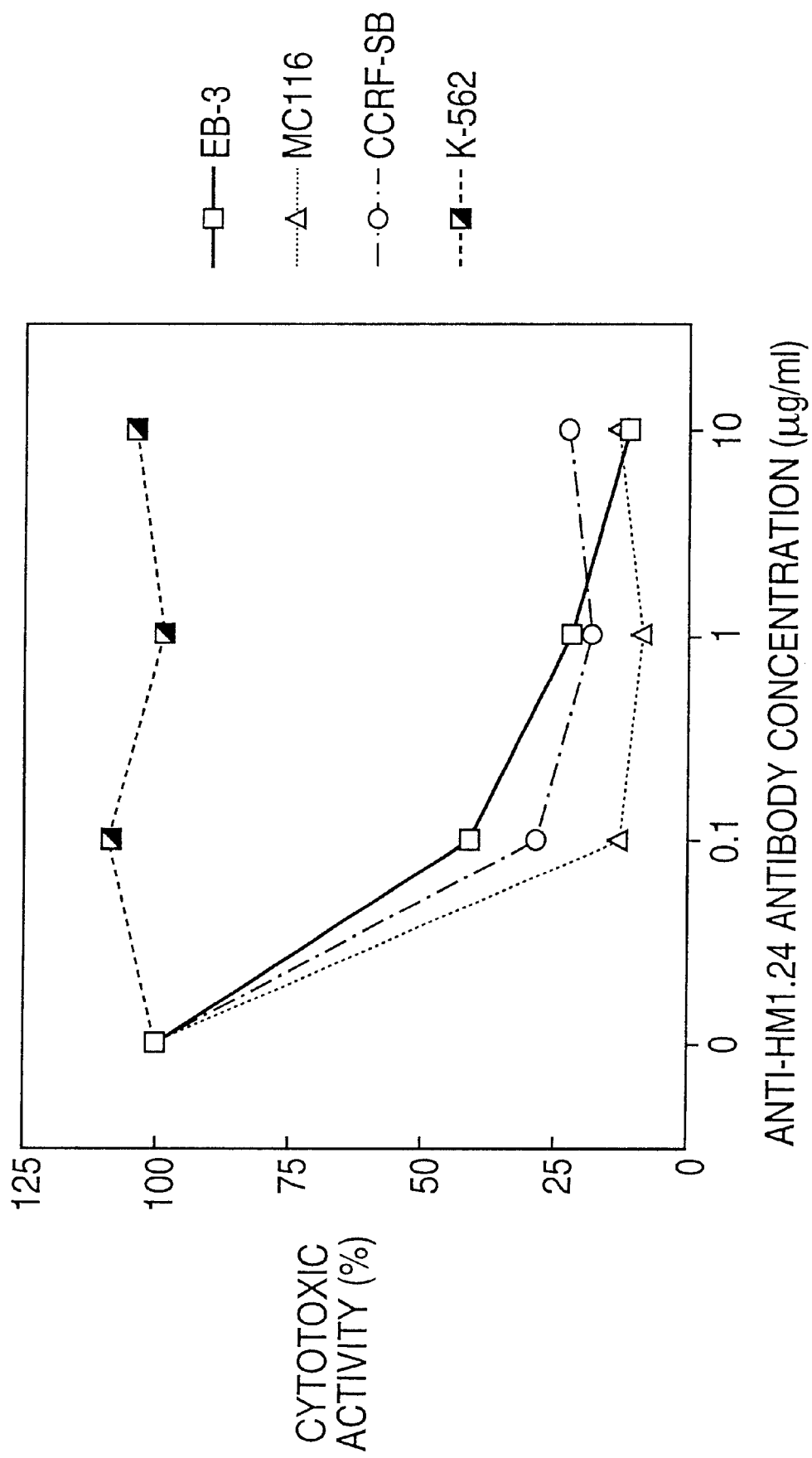
FIG. 25 is a graph showing that anti-HM1.24 antibody is exerting a cytotoxic effect to B cell tumor cell lines EB-3, MC116, and CCRF-SB in a dose-dependent manner.

The result revealed, as shown in FIGS. 24 and 25, that K562, that did not react with anti-HM1.24 antibody in the FCM analysis, exhibited no cytotoxicity either even when anti-HM1.24 antibody was added, whereas CCRF-CEM, CCRF-HSB-2, HPB-MLT, EB-3, MC116, and CCRF-SB, that reacted with anti-HM1.24 antibody, exhibited cytotoxicity in a manner dependent on the concentration of anti-HM1.24 antibody. This clarified that anti-HM1.24 antibody exhibits a CDC activity to a lymphatic tumor that has on the cell surface an antigen protein to which anti-HM1.24 antibody specifically binds.

Example 4

Antitumor Effects of Anti-HM1.24 Antibody on Mice Transplanted with a Human Lymphatic Tumor 1. Preparation of antibody to be administered 1-1. Preparation of anti-HM1.24 antibody The purified anti-HM1.24 antibody obtained in the above Example 1 was prepared at 1 mg/ml and 200 μg/ml in a filter-sterilized PBS(−) and was used for the following experiments.

1-2. Preparation of control mouse IgG2a

The purified antibody obtained in the above Example 2 was prepared at 1 mg/ml in a filter-sterilized PBS(−) and was used for the following experiments.

2. Antitumor effects of anti-HM1.24 antibody on mice transplanted with a human lymphatic tumor 2-1. Preparation of mice Transplanted with a human lymphatic tumor Mice transplanted with a human lymphatic tumor were prepared as follows. Acute lymphoblastic leukemia-derived CCRF-HSB-2 cells (ATCC CCL 120.1) that were subcultured in vivo using SCID mice (CLEA Japan) were prepared at $1 \times 10^8$ cells/ml in an RPMI1640 medium containing 10% fetal bovine serum (manufactured by GIBCO-BRL). The cell suspensions prepared as described above were subcutaneously injected into the abdomen of SCID mice (male, 6-week old) that each had previously received an intraperitoneal administration of 100 μl of anti-asialo GM1 (Wako Pure Chemical Industries, Ltd.) on the previous day.

2-2. Administration of antibody

On day 7 after the transplantation of the tumor, the diameter of the tumor at the site where the CCRF-HSB-2 of the above mice transplanted with a human lymphatic tumor was measured using calipers. After the volume of the tumor was calculated, the animals were grouped so that the mean tumor volume of each group was almost equal to one another (8 animals per group, 3 groups). From the same day, 100 μl of 1 mg/ml or 200 μg/ml of the anti-HM1.24 antibody or 1 mg/ml of the control mouse IgG2a prepared in the above 1 was intraperitoneally given to each group. The administration was conducted twice per week for a total of 19 times in a similar manner. During this period, the diameter of the tumor was measured using calipers twice per week and the volume of the tumor was calculated.

Figure 26:
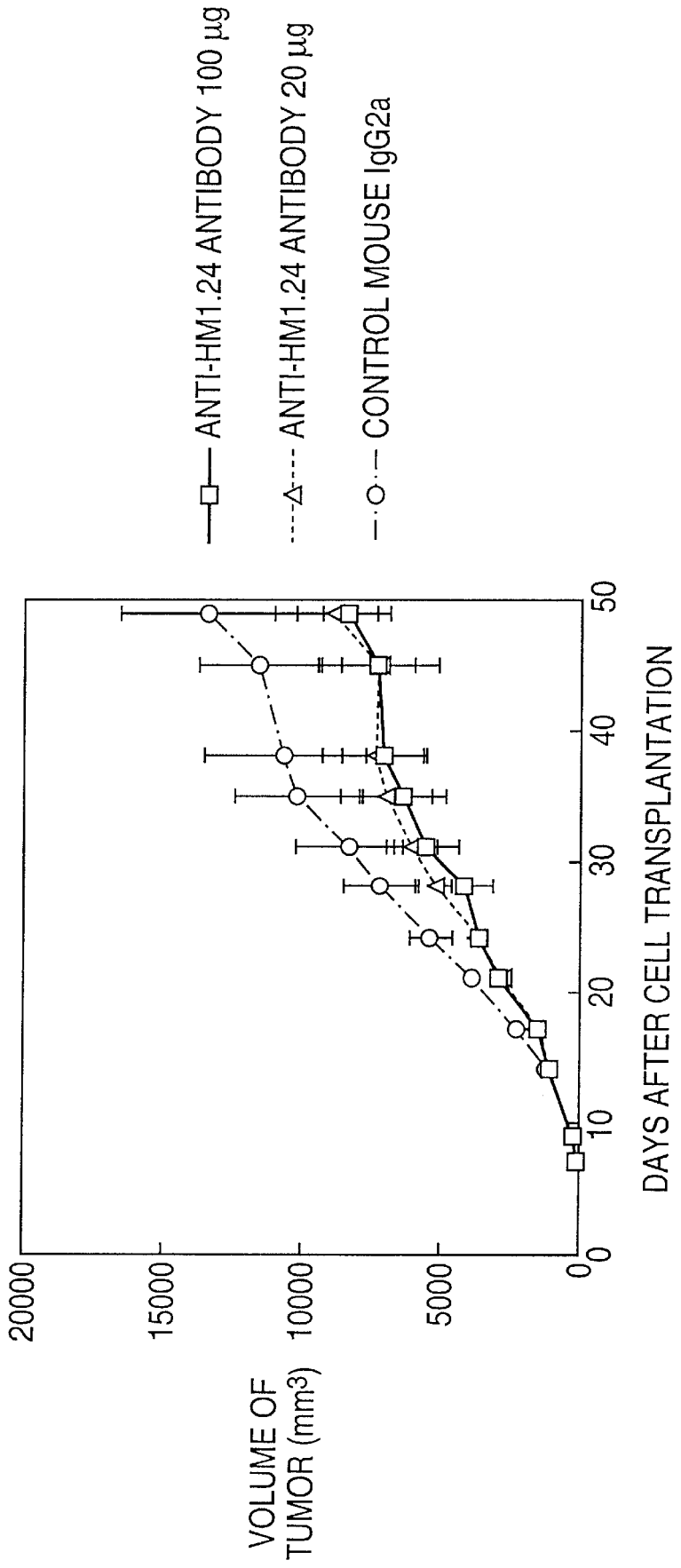
FIG. 26 is a graph showing that an increase in the volume of tumor is suppressed in the anti-HM1.24 antibody administration group as compared to the control mouse IgG2a administration group in mice transplanted with a human lymphatic tumor.

2-3. Evaluation of an antitumor effect of anti-HM1.24 antibody on mice transplanted with a human lymphatic tumor The antitumor effect of anti-HM1.24 antibody was evaluated by changes in the volume of tumor and the survival period of the mice. As a result, as shown in FIG. 26, an increase in the volume of the tumor was suppressed in the anti-HM1.24 antibody administration group as compared to the control mouse IgG2a administration group. Also as shown in FIG. 27, the extension of the survival period was observed in the anti-HM1.24 antibody administration group as compared to the control mouse IgG2a administration group. These facts indicated that anti-HM1.24 antibody has an antitumor effect on mice transplanted with a human lymphatic tumor.

Reference Example 1

Preparation of Hybridomas that Produce Mouse Anti-HM1.24 Monoclonal Antibody

In accordance with the method of Goto, T. et al., Blood (1994) 84, 1992–1930, hybridomas that produce mouse anti-HM1.24 monoclonal antibody were prepared.

A plasma cell line KPC-32 ($1 \times 10^7$) derived from the bone marrow of a patient with human multiple myeloma (Goto, T. et al., Jpn. J. Clin. Hematol. (1991) 32, 1400) was injected twice to the abdominal cavity of a BALB/c mouse (manufactured by Charles River) every six weeks.

Three days prior to sacrificing the animal, $1.5 \times 10^6$ KPC-32 were injected to the spleen of the mouse in order to further enhance the antibody-producing ability of the mouse (Goto, T. et al., Tokushima J. Exp. Med. (1990) 37, 89). After sacrificing the animal the spleen was extracted and the extracted organ was subjected to cell fusion with the myeloma cell SP2/0 according to the method of Groth, de St. & Schreidegger (Cancer Research (1981) 41, 3465).

By the Cell ELISA (Posner, M. R. et al., J. Immunol. Methods (1982) 48, 23) using KPC-32, the culture supernatant of the hybridoma was screened for antibody. $5 \times 10^4$ KPC-32 were suspended in 50 ml of PBS and then was aliquoted to a 96-well plate (U-bottomed, Corning, manufactured by Iwaki), which was then air-dried at 37° C. overnight. After blocking with PBS containing 1% bovine serum albumin (BSA), the culture supernatant of the hybridoma was added thereto and incubated at 4° C. for 2 hours. Then, peroxidase-labeled anti-mouse IgG goat antibody (manufactured by Zymed) was reacted at 4° C. for 1 hour. After washing, o-phenylene diamine solution (manufactured by Sumitomo Bakelite) was reacted at room temperature for 30 minutes.

Reaction was stopped by adding 2 N sulfuric acid and the absorbance was measured at 492 nm using the ELISA reader (manufactured by Bio-Rad). In order to remove the hybridoma that produce antibodies against human immunoglobulin, the culture supernatant of the positive hybridoma had previously been adsorbed to human serum and the reactivity to other cell lines was screened by ELISA. Positive hybridomas were selected, and their reactivity to various cells was investigated by flow cytometry. The last selected hybridoma clone was cloned twice and was injected to the abdominal cavity of a pristane-treated BALB/c mice and ascites were obtained therefrom.

Monoclonal antibodies were purified from the ascites of the mouse by ammonium sulfate precipitation and a Protein A affinity chromatography kit (Ampure Pa., manufactured by Amersham). The purified antibodies were labeled with FITC using the Quick Tag FITC biding kit (manufactured by Boehringer Mannheim).

As a result, monoclonal antibodies produced by 30 hybridoma clones reacted with KPC-32 and RPMI 8226. After cloning, the reactivity of the culture supernatant of these hybridomas with other cell lines or peripheral blood mononuclear cells was investigated.

Of them, 3 clones produced monoclonal antibodies that specifically reacted with the plasma cell. From among the 3 clones, a hybridoma clone that was most useful for flow cytometry analysis and had a CDC activity to RPMI 8226 was selected and designated as HM1.24. The subclass of the monoclonal antibody produced by this hybridoma was determined by an ELISA using a subclass-specific anti-mouse rabbit antibody (manufactured by Zymed). Anti-HM1.24 antibody had a subclass of IgG2a κ. The hybridoma HM1.24 that produces anti-HM1.24 antibody was internationally deposited under the provisions of the Budapest Treaty as FERM BP-5233 on Sep. 14, 1995 with the National Institute of Bioscience and Human-Technology, Agency of Industrial Science and Technology, of 1-3, Higashi 1-chome, Tsukuba city, Ibaraki pref., Japan.

Reference Example 2

Preparation of Humanized Anti-HM1.24 Antibody

Humanized anti-HM1.24 antibody was obtained in the following method.

From the hybridoma HM1.24 prepared in Reference example 1, total RNA was prepared by the conventional method. From this, cDNA encoding the V region of mouse antibody was synthesized and amplified by a polymerase chain reaction (PCR) method and the 5'-RACE method. A DNA fragment containing the gene encoding a mouse V region was obtained, which was ligated to each plasmid pUC cloning vector and then introduced into competent E. coli cells to obtain an E. coli transformant. The above plasmid was obtained from the transformant. The nucleotide sequence of the cDNA coding region in the plasmid was determined in the conventional method, and the complementarity determining region (CDR) of each V region was determined.

In order to construct a vector expressing chimeric anti-HM1.24 antibody, cDNA encoding a V region of each of the L chain and the H chain of a mouse anti-HM1.24 antibody was inserted to the HEF vector. Furthermore, in order to construct humanized anti-HM1.24 antibody, a V region CDR of a mouse anti-HM1.24 antibody was grafted to a human antibody by the CDR grafting method. The L chain of human antibody REI was used as the L chain of human antibody, FRs 1 to 3 of the human antibody HG3 were used for the framework regions (FRs) 1 to 3 of the H chain of human antibody, and FR4 of the human antibody JH6 was used for FR4. Some amino acids in the FR of the H chain V region were replaced so that the CDR-transplanted antibody could form a suitable antigen-binding site.

In order to express the gene of the L chain and the H chain of the thus constructed humanized anti-HM1.24 antibody in a mammalian cell, each gene was separately introduced into the HEF vector to construct a vector that expresses the L chain or the H chain of the humanized anti-HM1.24 antibody, respectively.

By simultaneously introducing these two expression vectors into the CHO cells, a cell line that produces humanized anti-HM1.24 antibody was established. The antigen binding activity and the binding inhibition activity to human amnion cell line WISH of humanized anti-HM1.24 antibody obtained by culturing this cell line were investigated by the Cell ELISA. The result indicated that the humanized anti-HM1.24 antibody has an antigen binding activity equal to chimeric antibody, and for the biding inhibition activity using a biotinylated mouse anti-HM1.24 antibody as well, it had an activity equal to chimeric antibody or mouse antibody.

Incidentally, E. coli having the plasmid that contains the DNA encoding the L chain V region and that for the H chain V region of chimeric anti-HM1.24 antibody have been internationally deposited under the provisions of the Budapest Treaty as Escherichia coli DH5α (pUC19-1.24L-gκ) and Escherichia coli DH5α (pUC19-1.24H-gγ1) on Aug. 29, 1996 with the National Institute of Bioscience and Human-Technology, Agency of Industrial Science and Technology, of 1-3, Higashi 1-chome, Tsukuba city, Ibaraki pref., Japan, as FERM BP-5646 and FERM BP-5644, respectively. Furthermore, E. coli having the plasmid that contains the DNA encoding the version a (SEQ ID NO: 2) of the L chain V region or that for the version r (SEQ ID NO:3) of the H chain V region of humanized anti-HM1.24 antibody have been internationally deposited under the provisions of the Budapest Treaty as Escherichia coli DH5α (pUC19-RVLa-AHM-gκ) and Escherichia coli DH5α (pUC19-RVHr-AHM-gγ1), respectively, on Aug. 29, 1996 with the National Institute of Bioscience and Human-Technology, Agency of Industrial Science and Technology, of 1-3, Higashi 1-chome, Tsukuba city, Ibaraki pref., Japan, as FERM BP-5645 and FERM BP-5643, respectively.

Furthermore, E. coli having the plasmid that contains the DNA encoding the version s (SEQ ID NO:4) of the H chain V region of humanized anti-HM1.24 antibody has been internationally deposited under the provisions of the Budapest Treaty as Escherichia coli DH5α (pUC19-RVHs-AHM-gγ1) on Sep. 29, 1997 with the National Institute of Bioscience and Human Technology, Agency of Industrial Science and Technology, of 1-3, Higashi 1-chome, Tsukuba city, Ibaraki pref., Japan, as FERM BP-6127.

Reference Example 3

Cloning of cDNA Encoding HM1.24 Antigen Protein cDNA encoding HM1.24 antigen protein specifically recognized by anti-HM1.24 antibody was cloned.

1. Construction of cDNA Library

1) Preparation of Total RNA

From the human multiple myeloma cell line KPMM2, total RNA was prepared according to the method of Chirgwin et al. (Biochemistry, 18, 5294 (1979)). Thus, 2.2×10$^8$ KPMM2 was completely homogenized in 20 ml of 4 M guanidine thiocyanate (manufactured by Nacalai Tesque Inc.). The homogenate was layered on a 5.3 M cesium chloride solution in a centrifuge tube, which was then centrifuged in a Beckman SW40 rotor at 31,000 rpm at 20° C. for 24 hours to precipitate RNA. The RNA precipitate was washed in 70% ethanol and then dissolved in 300 μl of 10 mM Tris-HCl (pH 7.4) containing 1 mM EDTA and 0.5% SDS. Pronase (manufactured by Boehringer) was added thereto to a concentration of 0.5 mg/ml and then was incubated at 37° C. for 30 minutes. The mixture was extracted with phenol and chloroform, and RNA was precipitated with ethanol. The RNA precipitate was then dissolved in 200 μl of 10 mM Tris-HCl (pH 7.4) containing 1 mM EDTA.

2) Preparation of poly(A)+RNA

Poly(A)+RNA was purified using as material 500 μg of the total RNA prepared as described above by the Fast Track 2.0 mRNA Isolation Kit (manufactured by Invitrogen) according to the regimen attached to the kit.

3) Construction of cDNA library

Double stranded cDNA was synthesized using as material 10 μg of the above poly(A)+RNA by the cDNA synthesis kit TimeSaver cDNA Synthesis Kit (manufactured by Pharmacia) according to the regimen attached to the kit, and was further ligated to the EcoRI adapter supplied in the kit using the Directional Cloning Toolbox (manufactured by Pharmacia) according to the regimen attached to the kit. The kination and the restriction enzyme NotI treatment of the EcoRI adapter were carried out according to the regimen attached to the kit. Furthermore, the adapter-added double stranded cDNA having a size of about 500 bp or greater was separated and purified using a 1.5% low melting point agarose gel (manufactured by Sigma) to obtain about 40 μl of adapter-added double stranded cDNA.

The adapter-added double stranded cDNA thus constructed was ligated using pCOS1 vector (Japanese Patent Application 8-255196) and T4 DNA ligase (manufactured by GIBCO-BRL) that had previously been treated with restriction enzymes EcoRI and NotI and alkaline phosphatase (manufactured by Takara Shuzo) to construct a cDNA library. The constructed cDNA library was transduced to an E. coli strain DH5α (manufactured by GIBCO-BRL) and consequently it was estimated to be an independent clone having a total size of about $2.5 \times 10^6$.

2. Cloning by the direct expression method

1) Transfection to COS-7 cells

About $5 \times 10^5$ clones of the above transduced E. coli were cultured in a 2-YT medium (Molecular Cloning: A Laboratory Manual, Sambrook et al., Cold Spring Harbor Laboratory Press (1989)) containing 50 μg/ml ampicillin to amplify cDNA, which was subjected to the alkali method (Molecular Cloning: A Laboratory Manual, Sambrook et al., Cold Spring Harbor Laboratory Press (1989)) to recover plasmid DNA from the E. coli. The plasmid DNA thus obtained was transfected to COS-7 cells by the electroporation method using the Gene Pulser instrument (manufactured by Bio-Rad).

Thus, 10 μg of the purified plasmid DNA was added to 0.8 ml of the COS-7 cell solution in which the cells had been suspended in PBS at $1 \times 10^7$ cells/ml, and the mixture was subjected to pulses of 1500 V and 25 μFD capacity. After a 10 minute recovery period at room temperature, the electroporated cells were cultured in a DMEM culture medium (manufactured by GIBCO-BRL) containing 10% fetal bovine serum (manufactured by GIBCO-BRL) under the condition of 37° C. and 5% $CO_2$ for 3 days.

2) Preparation of a panning dish

A panning dish on which mouse anti-HM1.24 antibody had been coated was prepared by the method of B. Seed et al. (Proc. Natl. Acad. Sci. U.S.A., 84, 3365–3369 (1987)). Thus, mouse anti-HM1.24 antibody was added to 50 mM Tris-HCl (pH 9.5) to a concentration of 10 μg/ml. Three milliliters of the antibody solution thus prepared was added to a cell culture dish with a diameter of 60 mm and was incubated at room temperature for 2 hours. After washing three times in 0.15 M NaCl solution, PBS containing 5% fetal bovine serum, 1 mM EDTA, and 0.02% $NaN_3$ was added to the dish. After blocking, it was used for the following cloning.

3) Cloning of cDNA library

The COS-7 cells transfected as described above were peeled off with PBS containing 5 mM EDTA. After washing the cells once in PBS containing 5% fetal bovine serum, they were suspended in PBS containing 5% fetal bovine serum and 0.02% $NaN_3$ to a concentration of about $1 \times 10^6$ cells/ml. The suspension was added to the panning dish prepared as described above and was incubated at room temperature for about 2 hours. After gently washing three times in PBS containing 5% fetal bovine serum and 0.02% $NaN_3$, plasmid DNA was recovered from the cells bound to the panning dish using a solution containing 0.6% SDS and 10 mM EDTA.

The recovered plasmid DNA was transduced into E. coli DH5α. After amplifying as described above, the plasmid DNA was recovered by the alkali method. The recovered plasmid DNA was transfected into COS-7 cells by the electroporation method and plasmid DNA recovered from the cells bound as described above. A similar procedure was repeated once, and the recovered plasmid DNA was digested with restriction enzymes EcoRI and NotI, thereby confirming the concentration of an insert having a size of about 0.9 kbp. Furthermore, E. coli cells in which a portion of the recovered plasmid DNA had been transduced were inoculated to a 2-YT agar plate containing 50 μg/ml of ampicillin. After culturing overnight, plasmid DNA was recovered from a single colony. It was digested with restriction enzymes EcoRI and NotI to obtain a clone p3.19 in which the size of the insert is about 0.9 kbp.

This clone was reacted using the PRISM, Dye Terminater Cycle Sequencing kit (manufactured by Perkin Elmer) according to the regimen attached to the kit, and the nucleotide sequence was determined using the ABI 373A DNA Sequencer (manufactured by Perkin Elmer). This nucleotide sequence and the corresponding amino acid sequence are shown in SEQ ID NO:1.

Industrial Applicability

The results of FCM analysis revealed that anti-HM1.24 antibody strongly reacted to most of the cells derived from human lymphatic tumors, indicating that in many of the lymphatic tumors, a polypeptide having an epitope recognized by anti-HM1.24 antibody is being strongly expressed. Furthermore, in mice transplanted with a human lymphatic tumor that reacts to anti-HM1.24 antibody, the administration of anti-HM1.24 antibody resulted in the suppression of an increase in tumor volume and furthermore the extension of the survival period. These facts indicate that anti-HM1.24 antibody or antibodies recognized by a polypeptide having an epitope recognized by anti-HM1.24 antibody have a cytotoxic activity to many lymphatic tumors, which thereby suggests that the antibody may be useful for the treatment of patients with a lymphatic tumor.

Reference to the microorganisms deposited under the Patent Cooperation Treaty, Rule 13-2, and the name of the Depository Institute.

Depository Institute
  Name: the National Institute of Bioscience and Human Technology, Agency of Industrial Science and Technology
  Address: 1-3, Higashi 1-chome, Tsukuba city, Ibaraki pref., Japan Microorganism (1)
  Name: *Escherichia coli* DH5α (pRS38-pUC19)
  Accession number: FERM BP-4434
  Date deposited: Oct. 5, 1993

Microorganism (2)
  Name: hybridoma HM1.24
  Accession number: FERM BP-5233
  Date deposited: Sep. 14, 1995

Microorganism (3)
  Name: *Escherichia coli* DH5α (pUC19-RVHr-AHM-gγ1)
  Accession number: FERM BP-5643
  Date deposited: Aug. 29, 1996

Microorganism (4)
  Name: *Escherichia coli* DH5α (pUC19-1.24H-gγ1)
  Accession number: FERM BP-5644
  Date deposited: Aug. 29, 1996

Microorganism (5)
  Name: *Escherichia coli* DH5α (pUC19-RVLa-AHM-gκ)

Accession number: FERM BP-5645
Date deposited: Aug. 29, 1996
Microorganism (6)
Name: *Escherichia coli* DH5α (pUC19-1.24L-gκ)
Accession number: FERM BP-5646
Date deposited: Aug. 29, 1996

Microorganism (7)

Name: *Escherichia coli* DH5α (pUC19-RVHs-AHM-gγ1)
Accession number: FERM BP-6127
Date deposited: Sep. 29, 1997

What is claimed is:

1. A method for the treatment of lymphatic tumors excluding myeloma comprising administering to a subject in need of such treatment an effective amount of an antibody that specifically binds to a protein having the amino acid sequence set forth in SEQ ID NO:5 and which antibody has a cytotoxic activity.

2. The method according to claim 1 wherein the lymphatic tumor is a T cell tumor.

3. The method according to claim 1 wherein the lymphatic tumor is a B cell tumor excluding myeloma.

4. The method according to claim 1 wherein the cytotoxic activity is an ADCC activity.

5. The method according to claim 1 wherein the cytotoxic activity is CDC activity.

6. The method according to claim 1 wherein the antibody is a monoclonal antibody.

7. The method according to claim 6 wherein the antibody is anti-HM1.24 antibody which is produced by the hybridoma deposited as FERM BP-5233.

8. The method according to claim 6 wherein the antibody has a human antibody constant region Cγ.

9. The method according to claim 8 wherein the human antibody constant region Cγ is Cγ1 or Cγ3.

10. The method according to claim 9 wherein the antibody is a chimeric antibody or a humanized antibody.

11. The method according to claim 10 wherein the chimeric antibody consists of the variable region of the anti-HM1.24 antibody which is produced by the hybridoma deposited as FERM BP-5233 and the human antibody constant region Cγ1 or Cγ3.

12. The method according to claim 10 wherein the humanized antibody consists of the variable region comprising CDRs of anti-HM1.24 antibody which is produced by the hybridoma deposited as FERM BP-5233 and the human antibody constant region Cγ1 or Cγ3.

\* \* \* \* \*

SEQUENCE LISTING

<160> NUMBER OF SEQ ID NOS: 8

<210> SEQ ID NO 1
<211> LENGTH: 1013
<212> TYPE: DNA
<213> ORGANISM: Homo sapiens
<220> FEATURE:
<223> OTHER INFORMATION: Nucleotide sequence of DNA coding for HM1.24 antigen
<221> NAME/KEY: CDS
<222> LOCATION: (23)..(562)

<400> SEQUENCE: 1

```
gaattcggca cgagggatct gg atg gca tct act tcg tat gac tat tgc aga      52
                         Met Ala Ser Thr Ser Tyr Asp Tyr Cys Arg
                           1               5                  10 gtg ccc atg gaa gac ggg gat aag cgc tgt aag ctt ctg ctg ggg ata      100
Val Pro Met Glu Asp Gly Asp Lys Arg Cys Lys Leu Leu Leu Gly Ile
                 15                  20                  25 gga att ctg gtg ctc ctg atc atc gtg att ctg ggg gtg ccc ttg att      148
Gly Ile Leu Val Leu Leu Ile Ile Val Ile Leu Gly Val Pro Leu Ile
             30                  35                  40 atc ttc acc atc aag gcc aac agc gag gcc tgc cgg gac ggc ctt cgg      196
Ile Phe Thr Ile Lys Ala Asn Ser Glu Ala Cys Arg Asp Gly Leu Arg
         45                  50                  55 gca gtg atg gag tgt cgc aat gtc acc cat ctc ctg caa caa gag ctg      244
Ala Val Met Glu Cys Arg Asn Val Thr His Leu Leu Gln Gln Glu Leu
     60                  65                  70 acc gag gcc cag aag ggc ttt cag gat gtg gag gcc cag gcc gcc acc      292
Thr Glu Ala Gln Lys Gly Phe Gln Asp Val Glu Ala Gln Ala Ala Thr
 75                  80                  85                  90 tgc aac cac act gtg atg gcc cta atg gct tcc ctg gat gca gag aag      340
Cys Asn His Thr Val Met Ala Leu Met Ala Ser Leu Asp Ala Glu Lys
                 95                 100                 105 gcc caa gga caa aag aaa gtg gag gag ctt gag gga gag atc act aca      388
Ala Gln Gly Gln Lys Lys Val Glu Glu Leu Glu Gly Glu Ile Thr Thr
            110                 115                 120 tta aac cat aag ctt cag gac gcg tct gca gag gtg gag cga ctg aga      436
Leu Asn His Lys Leu Gln Asp Ala Ser Ala Glu Val Glu Arg Leu Arg
        125                 130                 135 aga gaa aac cag gtc tta agc gtg aga atc gcg gac aag aag tac tac      484
Arg Glu Asn Gln Val Leu Ser Val Arg Ile Ala Asp Lys Lys Tyr Tyr
    140                 145                 150 ccc agc tcc cag gac tcc agc tcc gct gcg gcg ccc cag ctg ctg att      532
Pro Ser Ser Gln Asp Ser Ser Ser Ala Ala Pro Gln Leu Leu Ile
155                 160                 165                 170 gtg ctg ctg ggc ctc agc gct ctg ctg cag tgagatccca ggaagctggc        582
Val Leu Leu Gly Leu Ser Ala Leu Leu Gln
                175                 180 acatcttgga aggtccgtcc tgctcggctt ttcgcttgaa cattcccttg atctcatcag    642
ttctgagcgg gtcatggggc aacacggtta gcggggagag cacgggtag ccggagaagg     702
```

```
gcctctggag caggtctgga ggggccatgg ggcagtcctg ggtgtgggga cacagtcggg      762
ttgacccagg gctgtctccc tccagagcct ccctccggac aatgagtccc ccctcttgtc      822
tcccaccctg agattgggca tggggtgcgg tgtgggggc atgtgctgcc tgttgttatg       882
ggtttttttt gcggggggg ttgcttttt ctggggtctt tgagctccaa aaaataaac         942 acttcctttg agggagagca caccttaaaa aaaaaaaaa aaaaaaaaaa aaaaaaattc       1002
gggcggccgc c                                                           1013

<210> SEQ ID NO 2
<211> LENGTH: 379
<212> TYPE: DNA
<213> ORGANISM: Artificial Sequence
<220> FEATURE:
<223> OTHER INFORMATION: Description of Artificial Sequence: Nucleotide
      sequence of DNA encoding L chain V region version
      a of humanized anti-HM1.24 antibody
<221> NAME/KEY: sig_peptide
<222> LOCATION: (1)..(58)
<221> NAME/KEY: mat_peptide
<222> LOCATION: (58)..(378)
<221> NAME/KEY: CDS
<222> LOCATION: (1)..(378)

<400> SEQUENCE: 2 atg gga tgg agc tgt atc atc ctc tcc ttg gta gca aca gct aca ggt       48
Met Gly Trp Ser Cys Ile Ile Leu Ser Leu Val Ala Thr Ala Thr Gly
            -15                 -10                  -5 gtc cac tcc gac atc cag atg acc cag agc cca agc agc ctg agc gcc       96
Val His Ser Asp Ile Gln Met Thr Gln Ser Pro Ser Ser Leu Ser Ala
        -1   1               5                  10 agc gtg ggt gac aga gtg acc atc acc tgt aag gct agt cag gat gtg      144
Ser Val Gly Asp Arg Val Thr Ile Thr Cys Lys Ala Ser Gln Asp Val
    15                  20                  25 aat act gct gta gcc tgg tac cag cag aag cca gga aag gct cca aag      192
Asn Thr Ala Val Ala Trp Tyr Gln Gln Lys Pro Gly Lys Ala Pro Lys
30                  35                  40                  45 ctg ctg atc tac tcg gca tcc aac cgg tac act ggt gtg cca agc aga      240
Leu Leu Ile Tyr Ser Ala Ser Asn Arg Tyr Thr Gly Val Pro Ser Arg
                50                  55                  60 ttc agc ggt agc ggt agc ggt acc gac ttc acc ttc acc atc agc agc      288
Phe Ser Gly Ser Gly Ser Gly Thr Asp Phe Thr Phe Thr Ile Ser Ser
            65                  70                  75 ctc cag cca gag gac atc gct acc tac tac tgc cag caa cat tat agt      336
Leu Gln Pro Glu Asp Ile Ala Thr Tyr Tyr Cys Gln Gln His Tyr Ser
        80                  85                  90 act cca ttc acg ttc ggc caa ggg acc aag gtg gaa atc aaa c             379
Thr Pro Phe Thr Phe Gly Gln Gly Thr Lys Val Glu Ile Lys
    95                  100                 105

<210> SEQ ID NO 3
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence of DNA encoding H chain V region version
      r of humanized anti-HM1.24 antibody
<221> NAME/KEY: sig_peptide
<222> LOCATION: (1)..(58)
<221> NAME/KEY: mat_peptide
<222> LOCATION: (58)..(417)
<221> NAME/KEY: CDS
<222> LOCATION: (1)..(417)

<400> SEQUENCE: 3
```

```
atg gac tgg acc tgg agg gtc ttc ttc ttg ctg gct gta gct cca ggt     48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag     96
Ala His Ser Gln Val Gln Leu Val Gln Ser Gly Ala Glu Val Lys Lys
         -1   1               5                  10 cct ggg gcc tca gtg aag gtt tcc tgc aag gca tct gga tac acc ttc    144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt    192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt    240
Glu Trp Met Gly Ser Ile Phe Pro Gly Asp Gly Asp Thr Arg Tyr Ser
                 50                  55                  60 cag aag ttc aag ggc aga gtc acc atg acc gca gac aag tcc acg agc    288
Gln Lys Phe Lys Gly Arg Val Thr Met Thr Ala Asp Lys Ser Thr Ser
             65                  70                  75 aca gcc tac atg gag ctg agc agc ctg aga tct gag gac acg gcc gtg    336
Thr Ala Tyr Met Glu Leu Ser Ser Leu Arg Ser Glu Asp Thr Ala Val
         80                  85                  90 tat tac tgt gcg aga gga tta cga cga ggg ggg tac tac ttt gac tac    384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                      418
Trp Gly Gln Gly Thr Thr Val Thr Val Ser Ser
110                 115                 120

<210> SEQ ID NO 4
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence of DNA encoding H chain V region version
      s of anti-HM1.24 antibody
<221> NAME/KEY: sig_peptide
<222> LOCATION: (1)..(58)
<221> NAME/KEY: mat_peptide
<222> LOCATION: (58)..(417)
<221> NAME/KEY: CDS
<222> LOCATION: (1)..(417)

<400> SEQUENCE: 4 atg gac tgg acc tgg agg gtc ttc ttc ttg ctg gct gta gct cca ggt     48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag     96
Ala His Ser Gln Val Gln Leu Val Gln Ser Gly Ala Glu Val Lys Lys
         -1   1               5                  10 cct ggg gcc tca gtg aag gtt tcc tgc aag gca tct gga tac acc ttc    144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt    192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt    240
Glu Trp Met Gly Ser Ile Phe Pro Gly Asp Gly Asp Thr Arg Tyr Ser
                 50                  55                  60 cag aag ttc aag ggc aga gtc acc atc acc gca gac aag tcc acg agc    288
Gln Lys Phe Lys Gly Arg Val Thr Ile Thr Ala Asp Lys Ser Thr Ser
             65                  70                  75
```

```
aca gcc tac atg gag ctg agc agc ctg aga tct gag gac acg gcc gtg    336
Thr Ala Tyr Met Glu Leu Ser Ser Leu Arg Ser Glu Asp Thr Ala Val
        80                  85                  90 tat tac tgt gcg aga gga tta cga cga ggg ggg tac tac ttt gac tac    384
Tyr Tyr Cys Ala Arg Gly Leu Arg Arg Gly Gly Tyr Tyr Phe Asp Tyr
        95                 100                 105 tgg ggg caa ggg acc acg gtc acc gtc tcc tca g                      418
Trp Gly Gln Gly Thr Thr Val Thr Val Ser Ser
110             115                 120

<210> SEQ ID NO 5
<211> LENGTH: 180
<212> TYPE: PRT
<213> ORGANISM: Homo sapiens
<220> FEATURE:
<223> OTHER INFORMATION: Amino acid sequence of HM1.24 antigen

<400> SEQUENCE: 5

Met Ala Ser Thr Ser Tyr Asp Tyr Cys Arg Val Pro Met Glu Asp Gly
 1               5                  10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
            35                  40                  45

Asn Ser Glu Ala Cys Arg Asp Gly Leu Arg Ala Val Met Glu Cys Arg
        50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
        180

<210> SEQ ID NO 6
<211> LENGTH: 126
<212> TYPE: PRT
<213> ORGANISM: Artificial Sequence
<220> FEATURE:
<223> OTHER INFORMATION: Description of Artificial Sequence: Amino acid
      sequence of L chain V region version a of
      humanized anti-HM1.24 antibody

<400> SEQUENCE: 6

Met Gly Trp Ser Cys Ile Ile Leu Ser Leu Val Ala Thr Ala Thr Gly
                -15                 -10                 -5

Val His Ser Asp Ile Gln Met Thr Gln Ser Pro Ser Ser Leu Ser Ala
        -1   1              5                   10

Ser Val Gly Asp Arg Val Thr Ile Thr Cys Lys Ala Ser Gln Asp Val
        15                  20                  25
```

```
Asn Thr Ala Val Ala Trp Tyr Gln Gln Lys Pro Gly Lys Ala Pro Lys
 30              35                  40                  45

Leu Leu Ile Tyr Ser Ala Ser Asn Arg Tyr Thr Gly Val Pro Ser Arg
             50                  55                  60

Phe Ser Gly Ser Gly Ser Gly Thr Asp Phe Thr Phe Thr Ile Ser Ser
             65                  70                  75

Leu Gln Pro Glu Asp Ile Ala Thr Tyr Tyr Cys Gln Gln His Tyr Ser
         80                  85                  90

Thr Pro Phe Thr Phe Gly Gln Gly Thr Lys Val Glu Ile Lys
         95                 100                 105

<210> SEQ ID NO 7
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of H chain V region version r of
      humanized anti-HM1.24 antibody

<400> SEQUENCE: 7

Met Asp Trp Thr Trp Arg Val Phe Phe Leu Leu Ala Val Ala Pro Gly
             -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30              35                  40                  45

Glu Trp Met Gly Ser Ile Phe Pro Gly Asp Gly Asp Thr Arg Tyr Ser
             50                  55                  60

Gln Lys Phe Lys Gly Arg Val Thr Met Thr Ala Asp Lys Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
         95                 100                 105

Trp Gly Gln Gly Thr Thr Val Thr Val Ser Ser
110             115                 120

<210> SEQ ID NO 8
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence H chain V region version s of
      anti-HM1.24 antibody

<400> SEQUENCE: 8

Met Asp Trp Thr Trp Arg Val Phe Phe Leu Leu Ala Val Ala Pro Gly
             -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30              35                  40                  45

Glu Trp Met Gly Ser Ile Phe Pro Gly Asp Gly Asp Thr Arg Tyr Ser
```

```
                           50                      55                       60
Gln Lys Phe Lys Gly Arg Val Thr Ile Thr Ala Asp Lys Ser Thr Ser
                65                      70                      75

Thr Ala Tyr Met Glu Leu Ser Ser Leu Arg Ser Glu Asp Thr Ala Val
            80                      85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110                 115             120
```